(12) United States Patent
Meyerson et al.

(10) Patent No.: US 12,424,335 B2
(45) Date of Patent: Sep. 23, 2025

(54) AI BASED OPTIMIZED DECISION MAKING FOR EPIDEMIOLOGICAL MODELING

(71) Applicant: Cognizant Technology Solutions U.S. Corporation, College Station, TX (US)

(72) Inventors: Elliot Meyerson, San Francisco, CA (US); Olivier Francon, Sainte-Foy-lès-Lyon (FR)

(73) Assignee: Cognizant Technology Solutions U.S. Corporation, College Station, TX (US)

( * ) Notice: Subject to any disclaimer, the term of this patent is extended or adjusted under 35 U.S.C. 154(b) by 1123 days.

(21) Appl. No.: 17/355,971

(22) Filed: Jun. 23, 2021

(65) Prior Publication Data
US 2022/0013241 A1    Jan. 13, 2022

Related U.S. Application Data

(60) Provisional application No. 63/049,370, filed on Jul. 8, 2020.

(51) Int. Cl.
*G16H 50/80* (2018.01)
*G06N 3/044* (2023.01)
(Continued)

(52) U.S. Cl.
CPC ............ *G16H 50/80* (2018.01); *G06N 3/044* (2023.01); *G06N 3/08* (2013.01); *G16H 40/20* (2018.01);
(Continued)

(58) Field of Classification Search
CPC ........ G16H 50/80; G16H 40/20; G16H 50/00; G16H 50/20; G06N 3/044; G06N 3/08;
(Continued)

(56) References Cited

U.S. PATENT DOCUMENTS 5,140,530 A    8/1992   Guha
5,761,381 A    6/1998   Arci
(Continued)

FOREIGN PATENT DOCUMENTS

EP    0762294 A2   3/1997
EP    2422276      2/2012
(Continued)

OTHER PUBLICATIONS

International Search Report and Written Opinion issued in App. No. PCT/US2022/032656, mailing date Nov. 4, 2022, 9 pages.
(Continued)

*Primary Examiner* — Quoc A Tran
(74) *Attorney, Agent, or Firm* — Dawn-Marie Bey; Bey & Cotropia PLLC

(57) ABSTRACT

The present invention relates to an ESP decision optimization system for epidemiological modeling. ESP based modeling approach is used to predict how non-pharmaceutical interventions (NPIs) affect a given pandemic, and then automatically discover effective NPI strategies as control measures. The ESP decision optimization system comprises of a data-driven predictor, a supervised machine learning model, trained with historical data on how given actions in given contexts led to specific outcomes. The Predictor is then used as a surrogate in order to evolve prescriptor, i.e. neural networks that implement decision policies (i.e. NPIs) resulting in best possible outcomes. Using the data-driven LSTM model as the Predictor, a Prescriptor is evolved in a multi-objective setting to minimize the pandemic impact.

29 Claims, 20 Drawing Sheets

(51) Int. Cl.
  *G06N 3/045* (2023.01)
  *G06N 3/048* (2023.01)
  *G06N 3/08* (2023.01)
  *G06N 3/086* (2023.01)
  *G06N 5/01* (2023.01)
  *G06N 5/045* (2023.01)
  *G06N 20/10* (2019.01)
  *G06N 20/20* (2019.01)
  *G06Q 30/0204* (2023.01)
  *G06Q 50/26* (2024.01)
  *G16H 40/20* (2018.01)
  *G16H 50/00* (2018.01)
  *G16H 50/20* (2018.01)

(52) U.S. Cl.
  CPC ............. *G16H 50/00* (2018.01); *G16H 50/20* (2018.01); *G06N 3/045* (2023.01); *G06N 3/048* (2023.01); *G06N 3/086* (2013.01); *G06N 5/01* (2023.01); *G06N 5/045* (2013.01); *G06N 20/10* (2019.01); *G06N 20/20* (2019.01); *G06Q 30/0204* (2013.01); *G06Q 50/26* (2013.01)

(58) Field of Classification Search
  CPC .......... G06N 3/045; G06N 3/048; G06N 5/01; G06N 5/045; G06N 3/086; G06N 20/10; G06N 20/20; G06Q 30/0204; G06Q 50/26
  See application file for complete search history.

(56) References Cited

U.S. PATENT DOCUMENTS

| | | |
|---|---|---|
| 5,845,266 A | 12/1998 | Lupien et al. |
| 5,920,848 A | 7/1999 | Schutzer et al. |
| 5,930,780 A | 7/1999 | Hughes et al. |
| 6,240,399 B1 | 5/2001 | Frank et al. |
| 6,249,783 B1 | 6/2001 | Crone et al. |
| 6,941,287 B1 | 9/2005 | Vaidyanathan |
| 7,013,344 B2 | 3/2006 | Megiddo |
| 7,246,075 B1 | 7/2007 | Testa |
| 7,370,013 B1 | 5/2008 | Aziz et al. |
| 7,444,309 B2 | 10/2008 | Branke et al. |
| 8,065,244 B2 | 11/2011 | Chen et al. |
| 8,364,519 B1 | 1/2013 | Basu |
| 8,527,433 B2 | 9/2013 | Hodjat et al. |
| 8,639,545 B2 | 1/2014 | Cases |
| 8,768,811 B2 | 7/2014 | Hodjat et al. |
| 8,775,341 B1 | 7/2014 | Commons |
| 8,825,560 B2 | 9/2014 | Hodjat |
| 8,909,570 B1 | 12/2014 | Hodjat et al. |
| 8,918,349 B2 | 12/2014 | Hodjat et al. |
| 8,977,581 B1 | 3/2015 | Hodjat et al. |
| 9,002,759 B2 | 4/2015 | Hodjat et al. |
| 9,015,093 B1 | 4/2015 | Commons |
| 9,053,431 B1 | 6/2015 | Commons |
| 9,230,211 B1 | 1/2016 | Basu |
| 9,466,023 B1 | 10/2016 | Shahrzad et al. |
| 9,489,630 B2 | 11/2016 | Achin et al. |
| 9,605,529 B1 | 3/2017 | Venter |
| 9,678,487 B1 | 6/2017 | Basu |
| 9,785,886 B1 | 10/2017 | Andoni |
| 10,255,529 B2 | 4/2019 | Rabinovich |
| 10,268,953 B1 | 4/2019 | Fink et al. |
| 10,364,662 B1 | 7/2019 | Basu |
| 10,430,709 B2 | 10/2019 | Shahrzad et al. |
| 10,699,194 B2 | 6/2020 | David |
| 10,860,931 B1 | 12/2020 | Venter |
| 10,970,441 B1 | 4/2021 | Zhang |
| 11,003,997 B1 | 5/2021 | Blackwood |
| 11,087,261 B1 | 8/2021 | Basu |
| 2002/0019844 A1 | 2/2002 | Kurowski et al. |
| 2002/0080169 A1 | 6/2002 | Diederiks |
| 2003/0014379 A1 | 1/2003 | Saias |
| 2003/0149603 A1 | 8/2003 | Ferguson et al. |
| 2003/0158887 A1 | 8/2003 | Megiddo |
| 2004/0143559 A1 | 7/2004 | Ayala |
| 2004/0210545 A1 | 10/2004 | Branke et al. |
| 2004/0254901 A1 | 12/2004 | Bonabeau et al. |
| 2005/0033672 A1 | 2/2005 | Lasry et al. |
| 2005/0136480 A1 | 6/2005 | Brahmachari |
| 2005/0187848 A1 | 8/2005 | Bonissone et al. |
| 2005/0197875 A1 | 9/2005 | Kauffman |
| 2005/0198103 A1 | 9/2005 | Ching |
| 2005/0256760 A1 | 11/2005 | Siddhanti |
| 2006/0218107 A1 | 9/2006 | Young |
| 2006/0247973 A1 | 11/2006 | Mueller |
| 2007/0094161 A1 | 4/2007 | Calabro |
| 2007/0100907 A1 | 5/2007 | Bayer |
| 2007/0143198 A1 | 6/2007 | Brandes et al. |
| 2007/0143759 A1 | 6/2007 | Ozgur et al. |
| 2007/0150435 A1 | 6/2007 | Murakawa |
| 2007/0185990 A1 | 8/2007 | Ono et al. |
| 2008/0071588 A1 | 3/2008 | Eder |
| 2008/0228644 A1 | 9/2008 | Birkestrand et al. |
| 2009/0125370 A1 | 5/2009 | Blondeau et al. |
| 2009/0307638 A1 | 12/2009 | McConaghy |
| 2009/0327178 A1 | 12/2009 | Jacobson |
| 2010/0018293 A1 | 1/2010 | Monkowski |
| 2010/0030720 A1 | 2/2010 | Stephens |
| 2010/0111991 A1 | 5/2010 | Raitano |
| 2010/0182935 A1 | 7/2010 | David |
| 2010/0256795 A1 | 10/2010 | McLaughlin |
| 2010/0257228 A1 | 10/2010 | Staggs |
| 2010/0257605 A1 | 10/2010 | McLaughlin |
| 2010/0274736 A1 | 10/2010 | Hodjat et al. |
| 2010/0274742 A1 | 10/2010 | Hodjat et al. |
| 2010/0293119 A1 | 11/2010 | Ferringer et al. |
| 2011/0040596 A1 | 2/2011 | Chen |
| 2011/0161264 A1 | 6/2011 | Cantin |
| 2011/0246834 A1 | 10/2011 | Rajashekara |
| 2012/0239517 A1 | 9/2012 | Blondeau |
| 2012/0239592 A1 | 9/2012 | Esbensen |
| 2012/0313798 A1 | 12/2012 | Markram |
| 2013/0006901 A1 | 1/2013 | Cantin |
| 2013/0124440 A1 | 5/2013 | Hodjat et al. |
| 2013/0132042 A1 | 5/2013 | Chan |
| 2013/0138436 A1 | 5/2013 | Yu |
| 2013/0254142 A1 | 9/2013 | Hodjat |
| 2013/0311412 A1 | 11/2013 | Lazar |
| 2014/0006316 A1 | 1/2014 | Hodjat |
| 2014/0011982 A1 | 1/2014 | Marasco |
| 2014/0019388 A1 | 1/2014 | Kingsbury |
| 2014/0229362 A1 | 8/2014 | Hodjat |
| 2015/0046181 A1 | 2/2015 | Adjaoute |
| 2015/0136602 A1 | 5/2015 | Jovanovich |
| 2015/0242760 A1 | 8/2015 | Miao |
| 2015/0288573 A1 | 10/2015 | Baughman |
| 2015/0331908 A1 | 11/2015 | Duffy |
| 2015/0356461 A1 | 12/2015 | Vinyals |
| 2016/0048753 A1 | 2/2016 | Sussillo |
| 2016/0063359 A1 | 3/2016 | Szegedy |
| 2016/0232445 A1 | 8/2016 | Srinivasan |
| 2016/0242690 A1 | 8/2016 | Principe |
| 2016/0283563 A1 | 9/2016 | Hodjat |
| 2016/0307071 A1 | 10/2016 | Perronnin |
| 2016/0328253 A1 | 11/2016 | Majumdar |
| 2016/0329047 A1 | 11/2016 | Tur |
| 2016/0329407 A1 | 11/2016 | Takemura |
| 2016/0350671 A1 | 12/2016 | Morris, II et al. |
| 2016/0364522 A1 | 12/2016 | Frey |
| 2017/0001093 A1 | 1/2017 | Mollice |
| 2017/0060963 A1 | 3/2017 | Whittaker |
| 2017/0063908 A1 | 3/2017 | Muddu |
| 2017/0103172 A1 | 4/2017 | Fink |
| 2017/0109355 A1 | 4/2017 | Li |
| 2017/0116520 A1 | 4/2017 | Min |
| 2017/0132528 A1 | 5/2017 | Aslan |
| 2017/0148433 A1 | 5/2017 | Catanzaro |
| 2017/0192638 A1 | 7/2017 | Iscoe |
| 2017/0193366 A1 | 7/2017 | Miikkulainen |
| 2017/0193367 A1 | 7/2017 | Miikkulainen |

(56) References Cited

U.S. PATENT DOCUMENTS

| | | |
|---|---|---|
| 2017/0193403 A1 | 7/2017 | Iscoe |
| 2017/0213156 A1 | 7/2017 | Hammond |
| 2017/0256254 A1 | 9/2017 | Huang |
| 2017/0262737 A1 | 9/2017 | Rabinovich |
| 2017/0270225 A1 | 9/2017 | Chen et al. |
| 2017/0293849 A1 | 10/2017 | Hodjat et al. |
| 2017/0323219 A1 | 11/2017 | Shahrzad |
| 2017/0323636 A1 | 11/2017 | Xiao |
| 2018/0018590 A1 | 1/2018 | Szeto |
| 2018/0053092 A1 | 2/2018 | Hajizadeh |
| 2018/0114115 A1 | 4/2018 | Liang |
| 2018/0114116 A1 | 4/2018 | Liang |
| 2018/0157972 A1 | 6/2018 | Hu |
| 2018/0240041 A1 | 8/2018 | Koch |
| 2018/0293498 A1 | 10/2018 | Campos |
| 2018/0357552 A1 | 12/2018 | Campos |
| 2018/0357566 A1 | 12/2018 | Liu |
| 2018/0365557 A1 | 12/2018 | Kobayashi |
| 2018/0365564 A1 | 12/2018 | Huang |
| 2019/0065954 A1 | 2/2019 | Bittner, Jr. |
| 2019/0147298 A1 | 5/2019 | Rabinovich |
| 2019/0244108 A1 | 8/2019 | Meyerson |
| 2019/0332678 A1 | 10/2019 | Ishida |
| 2020/0311556 A1 | 10/2020 | Francon |
| 2021/0004676 A1 | 1/2021 | Jaderberg |
| 2021/0050116 A1* | 2/2021 | Sabeti ............ G06N 7/01 |
| 2021/0097443 A1 | 4/2021 | Li |
| 2021/0183515 A1* | 6/2021 | Neumann ......... G16H 50/70 |
| 2021/0312297 A1 | 10/2021 | Francon |
| 2022/0027744 A1 | 1/2022 | Krishnan |
| 2022/0027837 A1 | 1/2022 | D'Attilio |
| 2022/0326923 A1 | 10/2022 | Prashanth |

FOREIGN PATENT DOCUMENTS

| | | |
|---|---|---|
| EP | 2422278 | 2/2012 |
| JP | H0810804 | 1/1996 |
| JP | 08-110804 | 4/1996 |
| JP | H09114797 A | 5/1997 |
| JP | 2001325041 | 11/2001 |
| JP | 2003044665 | 2/2003 |
| JP | 2004240671 | 8/2004 |
| JP | 2004302741 | 10/2004 |
| JP | 2005190372 A | 7/2005 |
| JP | 2007052247 | 3/2007 |
| JP | 2007207173 | 8/2007 |
| JP | 2007522547 | 8/2007 |
| JP | 2008129984 A | 6/2008 |
| WO | WO 2005/073854 | 8/2005 |
| WO | 2010120440 A2 | 10/2010 |
| WO | WO 2010/127039 | 11/2010 |
| WO | WO 2010/127042 | 11/2010 |
| WO | 2017161233 | 9/2017 |
| WO | 2018211138 | 11/2018 |
| WO | 2018213840 | 11/2018 |
| WO | 2018223822 A1 | 12/2018 |
| WO | 2019081705 | 5/2019 |
| WO | WO 2019/217876 | 11/2019 |

OTHER PUBLICATIONS

Francon et al., "Effective Reinforcement Learning through Evolutionary Surrogate-Assisted Prescription", ACM, Jul. 12, 2020, retrieved on [Oct. 11, 2022]. Retrieved from the internet <URL: https://dl.acm.org/doi/pdf/10.1145/3377930.3389842>.

Miikkulainen et al., "From Prediction to Prescription: Evolutionary Optimization of Non-Pharmaceutical Interventions in the COVID-19 Pandemic", arxiv.org, Aug. 1, 2020, retrieved on [Oct. 11, 2022]. Retrieved from the internet <URL: https://arxiv.org/pdf/2005.13766.pdf>.

Alejandro Barredo Arrietz, et al., "Explainable Artificial Intelligence (XAI): Concepts, Taxonomies, Opportunities and Challenges Toward Responsible AI," https://arxiv.org/pdf/1910.10045.pdf, 2019.

European Parliamentary Research Service, "Understanding Algorithmic Decision-Making: Opportunities and Challenges," https://www.europarl.europa.eu/RegData/etudes/STUD/2019/624261/EPRS_STU(2019)624261_EN.pdf, 2019.

Blen M. Keneni, "Evolving Rule Based Explainable Artificial Intelligence for Decision Support System of Unmanned Aerial Vehicles," Evolving_Rule_Based_Explainable_Artificial_Intelli.pdf, 2018.

Riccardo Guidotti, et al., "A Survey of Methods for Explaining Black Box Models," https://dl.acm.org/doi/fullHtml/10.1145/3236009, 2018.

Ilya Loshchilov, "Surrogate-Assisted Evolutionary Algorithms," https://tel.archives-ouvertes.fr/tel-00823881/document, 2013.

Alan Diaz-Manriquez, et al., "A Review of Surrogate Assisted Multiobjective Evolutionary Algorithms," http://downloads.hidawi.com/journals/cin/2016/9420460.pdf, 2016.

Erwan Le Merrer, et al., "The Bouncer Problem: Challenges to Remote Explainability," https://arxiv.org/pdf/1910.01432.pdf, 2020.

Alain Chabrier, IBM, "Explaining Decision Optimization Prescriptions," https://medium.com/ibm-watson/explaining-decision-optimization-prescriptions-7103abbc44e5, 2019.

Zhiwei Zeng, et al., "Context-Based and Explainable Decision Making With Argumentation," http://ifaamas.org/Proceedings/aamas2018/opdfs/p1114.pdf, 2018.

Jakob Bossek, et al., "One-Shot Decision-Making With and Without Surrogates," https://arxiv.org/pdf/1912.08956v1.pdf, 2019.

Cynthia Rudin, "Stop Explaining Black Box Machine Learning Models for High Stakes Decision and Use Interpretable Models Instead," https://www.nature.com/articles/s42256-019-0048-x, 2019.

Maribel Lopez, "Preparing for AI Ethics and Explainability in 2020,"https://www.forbes.com/sites/maribellopez/2020/01/21/preparing-for-ai-ethics-and-explainability-in-2020/#15b37b022f6e, 2020.

Goodman, et al., "European Union (EU) regulations on algorithmic decision-making and a 'right to explanation,'" arXiv: 1606.08813v3, Aug. 2016.

Qiu, X et al., Quantifying Point-Prediction Uncertainty in Neural Networks via Residual Estimation with an I/O Kernel, in Proceedings of the Eighth International Conference on Learning Representations (ICLR) (2020).

Hodjat, B et al., PRETSL: Distributed Probabilistic Rule Evolution for Time-Series Classification, in Genetic Programming Theory and Practice XIV. Springer, 139-148 (2018).

Meyerson, E. et la., Discovering evolutionary stepping stones through behavior domination, in Proceedings of the Genetic and Evolutionary Computation Conference (GECCO 2017).

Miikkulainen, R et al., Sentient ascend: AI-based massively multivariate conversion rate optimization. In Proceedings of the Thirtieth Innovative Applications of Artificial Intelligence Conference. AAAI (2018).

Miikkulainen et al., Ascend by Evolv: AI-Based Massively Multivariate Conversion Rate Optimization, AI Magazine (2019).

Johnson et al., "Flavor-Cyber-Agriculture: Optimization of plant metabolites in an open-source control environment through surrogate modeling," PLOS One (2019), https://doi.org/10.1371/journal.pone.0213918.

Stanley, K. et al., "Designing neural networks through neuroevolution" Nature Machine Intelligence, vol. 1, p. 24-35 (Jan. 2019).

Risto Miikkulainen, "Creative AI Through Evolutionary Computation," arXiv: 1901.03775v2, Feb. 22, 2020.

Diesenroth, M. and Rasmussen, C. E., "PILCO: A model-based and data-efficient approach to policy search," in Proceedings of the 28th International Conference on Machine Learning (ICML) (ICML '11), pp. 465-472, 2011.

Ha, D. and Schmidhuber, Jr., "Recurrent World Models Facilitate Policy Evolution," in Advances in Neural Information Processing Systems 32 (NIPS '18), Curran Associates, Inc., Red Hook, NY, USA, pp. 2455-2467, 2018.

Wahlström, N., Schön, T. B., and Deisenroth, M. P., "From pixels to torques: Policy learning with deep dynamical models," arXiv preprint arXiv: 1502.02251, 2015.

Mnih, V., Kavukcuoglu, K., Silver, D., Rusu, A. A., Veness, J., Bellemare, M. G., Graves, A., Riedmiller, M., Fidjeland, A. K.,

(56) References Cited

OTHER PUBLICATIONS

Ostrovski, G., and others, "Human-level control through deep reinforcement learning," Nature 518, 7540, pp. 529-533, 2015.
Hasselt, H. V., "Double Q-learning," in Advances in Neural Information Processing Systems 23, J. D. Lafferty, C. K. I. Williams, J. Shawe-Taylor, R. S. Zemel, and A. Culotta (Eds.), Curran Associates, Inc., pp. 2613-2621, 2010.
Wang, Z., Schaul, T., Hessel, M., Van Hasselt, H., Lanctot, M., and De Freitas, "Dueling Network Architectures for Deep Reinforcement Learning, in Proceedings of the 33$^{rd}$ International Conference on Machine Learning (ICML) (ICML '16)," vol. 48, JMLR org., 1995-2003.
Mnih, V., Badia, A. P., Mirza, M., Graves, A., Lillicrap, T., Harley, T., Silver, D., and Kavukcuoglu, "Asynchronous methods for deep reinforcement learning, (ICML) (ICML '16)," pp. 1928-1937, 2016.
Schulman, J., Wolski, F., Dhariwal, P., Radford, A., and Klimov, O., "Proximal Policy Optimization Algorithms," CoRR abs/1707. 06347, 2017.
Houthooft, R., Chen, Y., Isola, P., Stadie, B., Wolski, F., Ho, O. J., and Abbeel, P., "Evolved policy gradients, on Advances in Neural Information Processing Systems 31," Curran Associates, Inc., pp. 5400-5409, 2018.
Khadka, et al., "Evolution-Guided Policy Gradient in Reinforcement Learning, 32$^{nd}$ Conference on Neural Information Processing Systems," 2018.
Pourchot, et al., "CEM-RL: Combining Evolutionary and Gradient-Based Methods for Policy Search," ICLR, 2019.
Application as filed for U.S. Appl. No. 16/424,686, filed.
Application as filed for U.S. Appl. No. 16/502,439, filed.
Application as filed for U.S. Appl. No. 16/879,934, filed May 21, 2020.
Hodjat, et al., "Chapter 5: Introducing an Age-Varying Fitness Estimation Function," Genetic Programming Theory and Practice X, Ed. Riolo, et al., Springer, Apr. 19, 2013, pp. 59-71.
Li, Xiaodong and Kirley, Michael, "The Effects of Varying Population Density in a Fine-Grained Parallel Genetic Algorithm," 2002, CEC'02, Proceedings of the 2002 Congress on Evolutionary Computation, vol. 2, IEEE, 2002.
Fidelis, Marcos Vinicius, Heitor S. Lopes, and Alex A. Freitas, "Discovering Comprehensible Classification Rules With a Genetic Algorithm," Proceedings of the 2000 Congress on Evolutionary Computation, vol. 1, IEEE, 2000.
International Search Report and Written Opinion for PCT Application No. PCT/US2008/82876, Dec. 23, 2008, 8 pp.
Koza, J. R., "Genetic Programming: On the Programming of Computers by Means of Natural Selection," Dec. 1992, MIT Press, pp. 1-609.
Extended European Search Report for EP Application No. EP 08847214, 9 pp.
Enee, Gilles, et al., "Classifier Systems Evolving Multi-Agent System With Distributed Elitism," Proceedings of the 1999 Congress on Evolutionary Computation (CEC'99), vol. 3:6, Jul. 1999, pp. 1740-1746.
Tanev, I., et al., "Scalable Architecture for Parallel Distributed Implementation of Genetic Programming on Network of Workstations," J. Systems Architecture, vol. 47, Jul. 2001, pp. 557-572.
Streichert, F., "Introduction to Evolutionary Algorithms," paper to be presented Apr. 4, 2002 at the Frankfurt MathFinance Workshop, Mar. 30, 2002, Frankfurt, Germany, XP55038571, 22 p., Retrieved from the Internet: http://www.ra.cs.uni-tuegingen.de/mitarb/streiche/publications/Introduction_to_E_volutionary_Algorithms.pdf.
Written Opinion from Singapore Patent Office in related application SG 201003127-6, Jun. 16, 2011, 9 pp.
Exam Report for related application AU 2008323758, Apr. 20, 2012, 2 pp.
Sakauchi, et al., Unifine: A Next Generation Financial Solution System of Nihon Unisys Ltd., Technology Review 'Unisys,' Japan, Nihon Unisys Ltd., Feb. 28, 2006, vol. 25, No. 4, pp. 14-15.
Office Action from JP 2010-533295, dated Apr. 16, 2013, 12 pp.
Laumanns, Marco, et al., "A Unified Model for Multi-Objective Evolutionary Algorithms with Elitism," IEEE, pp. 46-53, 2000.
Ahn, Change Wook, et al., "Elitism-Based Compact Genetic Algorithms," IEEE, Transactions on Evolutionary Computation, vol. 7, No. 4, pp. 367-385, 2003.
Hornby, Gregory S., "The Age-Layered Population Structure (ALPS) Evolutionary Algorithm," ACM, GECCO '09, 7 pp., 2009.
Hornby, G. S., "ALPS: The Age-Layered Population Structure for Reducing the Problem of Premature Convergence," GECCO '06, Seattle, Jul. 2006, authored by an employee of the U.S. Government, therefore in the public domain, 8 pp.
Hornby, G. S. "A Steady-State Version of the Age-Layered Population Structure EA," Chapter 1 of Genetic Programming Theory and Practice VII, Riolo, et al., editors, Springer 2009, 16 pp.
Hornby, G. S., "Steady-State ALPS for Real-Valued Problems," GECCO '09, Montreal, Jul. 2009, Assoc. of Computing Machinery, 8 pp.
Idesign lab, "ALPS—The Age-Layered Population Structure," UC Santa Cruz web article printed Mar. 17, 2011, 3 pp., http://idesign.ucsc.edu/projects/alsp.html.
Gaspar-Cunha, A., et al., "A Multi-Objective Evolutionary Algorithm Using Neural Networks to Approximate Fitness Evaluations," Int'l. J. Computers, Systems and Signals, 6(1), pp. 18-36, 2005.
Kosorukoff, A., "Using Incremental Evaluation and Adaptive Choice of Operators in a Genetic Algorithm," Proc. Genetic and Evolutionary Computation Conference, GECCO, Sep. 2002, 7 pp.
Nelson, A., "Fitness Functions in Evolutionary Robotics: A Survey and Analysis," Robotics and Autonomous Systems 57, 2009, 345-370.
Wu, A. S., et al., "An Incremental Fitness Function for Partitioning Parallel Tasks," Proc. Genetic and Evolutionary Computation Conf., Aug. 2001, 8 pp.
Whitehead, B. A., "Genetic Evolution of Radial Basis Function Coverage Using Orthogonal Niches," IEEE Transactions on Neural Networks, 7:6, Nov. 1996, 1525-28.
Bui, L. T., et al., "Local Models: An Approach to Distributed Multi-Objective Optimization," Computational Optimization and Applications, vol. 42, No. 1, Oct. 2007, pp. 105-139.
Castillo, Tapia M. G., et al., "Applications of Multi-Objective Evolutionary Algorithms in Economics and Finance: A Survey," Proc. IEEE Congress on Evolutionary Computation, Sep. 2007, pp. 532-539.
Ducheyne, E., et al., "Is Fitness Inheritance Useful for Real-World Applications?," Evolutionary Multi-Criterion Optimization, ser. LNCS 2631, Spring 2003, pp. 31-42.
Gopalakrishnan, G., et al., "Optimal Sampling in a Noisy Genetic Algorithm for Risk-Based Remediation Design, Bridging the Gap: Meeting the World's Water and Environmental Resources Challenges," Proc. World Water Congress, 2001, 8 pp.
Juille, H., "Evolution of Non-Deterministic Incremental Algorithms as a New Approach for Search in State Spaces, Proc. 6$^{th}$ Int'l. Conf. on Genetic Algorithms," 1995 8 pp.
International Search Report mailed Jul. 2, 2010 in PCT/US10/32847.
International Search Report mailed Jun. 29, 2010 in PCT/US10/32841.
Sacks, J., et al., "Design and Analysis of Computer Experiments," Statistical Science, 4:4, 1989, 409-435.
Torresen, J., "A Dynamic Fitness Function Applied to Improve the Generalisation When Evolving a Signal Processing Hardware Architecture," Proc. EvoWorkshops, 2002, 267-299 (12 pp.).
Bartlett II, J. E., et al., "Organizational Research: Determining Appropriate Sample Size in Survey Research," IT, Learning, and Performance Journal, 19(1), Spring 2001, 8 pp.
Fitzpatrick, J. M., et al., "Genetic Algorithm in Noisy Environments," Machine Learning 3:101-120, May 1988.
Leon, C., et al., "Parallel Hypervolume-Guided Hyperheuristic for Adapting the Multi-Objective Evolutionary Island Model," Proc. 3$^{rd}$ Int'l. Workshop on Nature Inspired Cooperative Strategies for Optimization Studies in Computational Intelligence, vol. 236, Nov. 2008, pp. 261-272.

(56) References Cited

OTHER PUBLICATIONS

Lopez, Jaimes A., et al., "MRMOGA: Parallel Evolutionary Multiobjective Optimization Using Multiple Resolutions," Proc. IEEE Congress on Evolutionary Computation, vol. 3, Sep. 2005, pp. 2294-2301.
Davarynejad, M., et al., "A Novel General Framework for Evolutionary Optimization: Adaptive Fuzzy Fitness Granulation," CEC, Sep. 2007, 6 pp.
Davarynejad, M., "Fuzzy Fitness Granulation in Evolutionary Algorithms for Complex Optimization," Master of Science Thesis, Ferdowsi Univ. of Mashhad, Jun. 2007, 30 pp.
Salami, M., et al., "A Fast Evaluation Strategy for Evolutionary Algorithms," Applied Soft Computing 2/3F (2003), 156-173.
M.-R. Akbarzadeh-T., et al., "Friendship Modeling for Cooperative Co-Evolutionary Fuzzy Systems: A Hybrid GA-GP Algorithm," Proc. $22^{nd}$ Int'l. Conf. of N. American FIPS, Jul. 2003, pp. 61-66.
Mouret, J. B., et al., "Encouraging Behavioral Diversity in Evolutionary Robotics: An Empirical Study," MIT, Evolutionary Computation, 20(1):91-133, 2012.
Myers, "Raymond H. and Montgomery, Douglas C., Response Surface Methodology: Process and Product Optimization Using Designed Experiments," John Wiley and Sons, Inc., New York, 1995.
Poli, R., et al., "Genetic Programming: An Introductory Tutorial and a Survey of Techniques and Applications," Univ. Essex School of Computer Science and Electronic Engineering Technical Report No. CES-475, Oct. 2007, 112 pp.
Georgilakis, P. S., "Genetic Algorithm Model for Profit Maximization of Generating Companies in Deregulated Electricity Markets," Applied Artificial Intelligence, Jul. 2009. 23:6, 538-552.
Refaeilzadeh, P., et al., "Cross Validation," entry, Encyclopedia of Database Systems, eds. Ozsu and Liu, Springer, 2009, 6 pp.
Remde, S., et al., "Evolution of Fitness Functions to Improve Heuristic Performance," LION, Dec. 8-10, 2007 II, LNCS 5313, pp. 206-219.
Schoreels, C., "Agent Based Genetic Algorithm Employing Financial Technical Analysis for Making Trading Decisions Using Historical Equity Market Data," IEEE/WIC/ACM International Conference on Intelligent Agent Technology (IAT2004), Beijing, China, Sep. 20-24, 2004, pp. 421-424.
Bongard, J. C., et al., "Guarding Against Premature Convergence While Accelerating Evolutionary Search," GECCO '10: Proceedings of the $12^{th}$ Annual Conference on Genetic and Evolutionary Computation, 8 pp. (2010).
Gorunescu, et al., "Evolutionary strategy to develop learning-based decision systems, Application to breast cancer and liver fibrosis stadiallization" [online], Jun. 2014 [retrieved on May 21, 2020], Journal of Biomedical Informatics, vol. 49, pp. 1-32, Retrieved from the Internet: https://reader.elsevier.com/reader/sd/pii/S1532046414000173?token=E3DB70CBA3796F20A3C0B08ABA8E0657EED29D4423C65CF9959714AC34AD580F5755F248C38C14CEBE59D726C456A820.
Kaelbling, et al., Reinforcement Learning: A Survey [online], 1996 [retrieved May 21, 2020], Journal of Artificial Intelligence Research, vol. 4, pp. 237-285, Retrieved from the Internet: https://www.cs.cmu.edu/~tom/10701_sp11/slides/Kaelbling.pdf.
International Search Report and Written Opinion for PCT App. No. PCT/US20/25046, dated Jun. 23, 2020, 9 pp.
Risto Miikkulainen, "Creative AI Through Evolutionary Computation: Principles and Examples," SN Computer Science, 2:163, 2021, https://doi.org/10.1007/s42979-021-00540-9, 7 pp.
Risto Miikkulainen, et al., "From Prediction to Prescription: Evolutionary Optimization of Non-Pharmaceutical Interventions in the COVID-19 Pandemic," ar Xiv: 2005.13766v3, Aug. 1, 2020, 34 pp.
Risto Miikkulainen, et al., "From Prediction to Prescription: Evolutionary Optimization of Nonpharmaceutical Interventions in the COVID-19 Pandemic," IEEE Transactions on Evolutionary Computation, vol. 25, No. 2, Apr. 2021, 16 pp.
CS412 KL-divergence, computer science, Illinois university. 2017 (Year: 2017).

"CS 224D: Deep Learning for NLP, Lecture Notes: Part IV", 12 pp., Spring, 2015, 12 pages.
"CS 224D: Deep Learning for NLP, Lecture Notes: Part V", 6 pp., Spring, 2015, 6 pages.
"Revisiting Knowledge Distillation: A Teacher-Free Framework," ICLR 2020, 15 pp.
"CS 224D: Deep Learning for NLP, Lecture Notes: Part III". 14 pp., Spring, 2016.
Jun. 22, 2011 Office Action in U.S. Appl. No. 12/267,287, 16 pp.
Aug. 1, 2012 Office Action in U.S. Appl. No. 13/443,546, 12 pp.
Aditya Rawal and Risto Miikkulainen, "From Nodes to Networks: Evolving Recurrent Neural Networks," GECCO '18, Jul. 15-19, 2018, 8 pages, Kyoto, Japan.
Ajjad Abbasi, et al., "Modeling Teacher-Student Techniques in Deep Neural Networks for Knowledge Distillation," Computer Science, 2020 International Conference on Machine Vision and Image Processing (MVTP), 2020, 6 pp.
Al-Haj Baddar, "Finding Better Sorting Networks," Dissertation to Kent State University for PhD, May 2009, 86 pages.
Alesawy et al., Elliptic Curve Diffie-Hellman Random Keys Using Artificial Neural Network and Genetic Algorithm for Secure Data over Private Cloud, Inform. Technol. J., 15 (3): 77-83, 2016 (thru ResearchGate); Total pages: 9 (Year: 2016).
Alex Castrounis, Innoarchtech, "Production vs. Development AI and Machine Learning,"published by O'Reilly Media, Copyright InnoArchiTech LLC 2020, 24 pages.
Alex Castrounis, Innoarchtech, "Advanced Analytics Packages, Frameworks, and Platforms," 29 pages, published by O'Reilly Media, Copyright InnoArchiTech LLC 2020.
Alex Castrounis, Innoarchtech, "Python vs. R for AI, Machine Learning, and Data Science," published by O'Reilly Media, Copyright InnoArchiTech LLC 2020, 27 pages.
Anooj, "Clinical decision support system: Risk level prediction of heart disease using weighted fuzzy rules", 2012 (Year: 2012). 14 pages.
Ares "A soft computing framework for classifying time series based on fuzzy sets of events", 2015 (Year: 2015). 20 pages.
Atin Sood, et al., "NEUNETS: An Automated Synthesis Engine for Neural Network Design," arXiv: 1901.06261v1, Jan. 17, 2019, 14 pp.
AU 2010241594—Examination Report dated Oct. 8, 2013, 3 pages.
AU 2010241597—Examination Report dated Nov. 4, 2013, 4 pages.
Barret Zoph, et al., "Neural Architecture Search With Reinforcement Learning," arXiv: 1611.01578v2, Feb. 15, 2017, 16 pp.
Berg "Fuzzy Classification Using Probability-Based Rule Weighting", IEEE, 2002 (Year: 2002). 6 pages.
Bergstra, et al., (2013), "Hyperopt: A Python Library for Optimizing the Hyperparameters of Machine Learning Algorithms," Proceedings of the 12th Python in Science Conference (SCIPY 2013).
Bilen et al. "Integrated Perception with Recurrent Multi-Task Neural Networks", NIPS, 2016, pp. 9.
Bilen,et al.,"Integrated perception with Reccurrent Multi-Task Neural Networks," NIPS 2016 ,9 pp.
Bredeche et al., "On-Line , On-Board Evolution of Robot Controllers", Artifical Evolution: 9th International Conference, Evolution Artificielle , EA, Strasbourg, France, vol. 5975, (20090000), pp. 110-121, URL: https://dl.acm.org/citation.cfm?id=1883723. 1883738, (Mar. 15, 2019), XP019146179.
Bredeche, Nicolas, et al., "On-line, on-board evolution of robot controllers," International Conference on Artificial Evolution, Springer, Berlin, Heidelberg, 13 pages, 2009.
Caruana, R. Multitask learning. In Learning to learn, pp. 95-133. Springer US, 1998, (Year: 1998).
Chenglin Yang, et al., "Snapshot Distillation: Teacher-Student Optimization in One Generation," arXiv: 1812.00123v1, Dec. 1, 2018, 10 pp.
Deb, et al., "A fast and elitist multiobjective genetic algorithm: NSGA-II," IEEE Transactions on Evolutionary Computation, 6(2), 2002, pp. 182-197.
Derrick Mwiti, "Research Guide: Model Distillation Techniques for Deep Learning" [online], Nov. 20, 2019 [retrieved on Oct. 5, 2020],

(56) References Cited

OTHER PUBLICATIONS 17 pp., Retrieved From the Internet: https://heartbeat.fritz.ai/research-guide-model-distillation-techniques-for-deep-learmng-4al00801c0eb.
Devin, Coline, et al., "Learning Modular Neural Network Policies for Multi-Task and Multi-Robot Transfer," arXiv:1609.07088vl, Sep. 22, 2016, 8 pp.
Di Gao, et al., "Private Knowledge Transfer via Model Distillation with Generative Adversarial Networks," arXiv:2004.0463lvl, Apr. 5, 2020, 8 pp.
Dong, "Multi-Task Learning for Multiple Language Translation," in Proc. of ACL, pp. 1723-1732, 2015.
E. Meyerson and R. Miikkulainen, "Beyond Shared Hierarchies: Deep Multitask Learning Through Soft Layer Ordering," ICLR, 14 pages, 2018.
Esparcia-Alcazar et al. "Evolving Recurrent Neural Network Architectures by Genetic Programming", 1997, pp. 6, https://citeseerx.ist.psu.edu/viewdoc/download?doi=10.1.1.40.226&rep=rep1&type=pdf.
Fernando et al., "Pathnet: Evolution channels gradient descent in super neural networks," arXiv preprint arXiv:1701.08734 (2017), 16 pages.
Freitas, A. "A review of evolutionary algorithms for data mining." Soft Computing for Knowledge Discovery and Data Mining. Springer US, 2008. 79-111.
Galea, "Iterative vs Simultaneous Fuzzy Rule Induction", IEEE, 2005 (Year: 2005). 6 pages.
Garcia-Pedrajas et al., "COVNET: A Cooperative Coevolutionary Model for Evolving Artificial Neural Networks", IEEE Transactions on Neural Networks, vol. 14, No. 3, (2003). (Year: 2003) 22 pages.
Garcia-Pedrajas, et al., "Cooperative Coevolution of Artificial Neural Network Ensembles for Pattern Classification," IEEE Transactions on Evolutionary Computation, vol. 9, No. 3, 32 pages, Jun. 3, 2005.
Garcia-Pedrajas, et. al., "Cooperative-Coevolution-of-Artificial-Neural-Networks", 2005, 32 pages.
Gaurav Kumar Nayak, et al., "Zero-Shot Knowledge Distillation in Deep Networks," arXiv: 1905.08114vl, May 20, 2019, 17 pp.
Golovin, e tal., "Google Vizier: A Service for Black-Box Optimization," Proceedings of the 23rd ACM SIGKDD International Conference on Knowledge Discovery and Data Mining, pp. 1487-1495, 2017.
Gomes et al., "Devising Effective Novelty Search Algorithms: A Comprehensive Empirical Study," Madrid, Spain, Copyright Jul. 11-15, 2015, ACM, 8 pages.
Gomes et al., "Evolution of Swarm Robotics Systems with Novelty Search," published in Swarm Intelligence, vol. 7, Issue 2, ANTS Special Issue, Copyright Sep. 2013, pp. 115-144.
Gomes et al., "Progressive Minimal Criteria Novelty Search," Lisboa, Portugal, cited in Advances in Artificial Intelligence, Springer-Verlag Berlin Heidelberg, Copyright 2012, pp. 281-290.
Gonzalez, et al., "Evolving Loss Functions With Multivariate Taylor Polynomial Parameterization," Version 2, published arXiv: 2002.00059v2), Feb. 10, 2020, 8 pages.
Gonzalez, et al., "Evolving Loss Functions With Multivariate Taylor Polynomial Parameterizations," Version 1, published arXiv: 2002.00059v1, Jan. 31, 2020. 12 pages.
Gonzalez, et al., "Optimizing Loss Functions Through Multivariate Taylor Polynomial Parameterization," Version 3 (published arXiv:2002.00059v3), Jun. 6, 2020, 13 pages.
Gupta et al., "An Overview of methods maintaining Diversity in Generic Algorithms," International Journal of Emerging Technology and Advanced Engineering, vol. 2, Issue 5, New Delhi, India, May 2012, pp. 56-60.
Pan et al ("A Classification-Based Surrogate-Assisted Evolutionary Algorithm for Expensive Many-objective Optimization" Feb. 2019) (Year: 2019).
Yousefi, N., Georgiopoulos, M. and Anagnostopoulos, G.C., 2015. Multi-task learning with group-specific feature space sharing. In Machine Learning and Knowledge Discovery in Databases: European Conference, ECML PKDD 2015, Porto, Portugal, Sep. 7-11, 2015, Proceedings, Part II 15 (pp. 120-136). Springer International Publishing.
Stanley, 2002, "Evolving Neural Networks Through Augmenting Topologies" (Year: 2002).
Cui et al, Oct. 2018, "Evolutionary Stochastic Gradient Descent for Optimization of Deep Neural Networks" (Year: 2018).
Jaimes & Coello, 2005, "MRMOGA: Parallel Evolutionary Multiobjective Optimization using Multiple Resolutions" (Year: 2005).
Cruz-Ramirez, 2010, "Memetic pareto differential evolutionary artificial neural networks to determine growth multi-classes in predictive microbiology" (Year: 2010).
Cruz-Ramirez et al, 2011, "Selecting the Best Artificial Neural Network Model from a Multi-Objective Differential Evolution Pareto Front" (Year: 2011).
Jin & Sendhoff, 2008, "Pareto-Based Multiobjective Machine Learning: An Overview and Case Studies" (Year: 2008).
Storsveen et al, 2008, "Evolving a 2D Model of an Eye using CPPNs" (Year: 2008).
Shi, 2008, "An Empirical Comparison of Evolution and Coevolution for Designing Artificial Neural Network Game Players" (Year: 2008).
Garciarena et al, Jul. 2018, "Evolved GANs for generating Pareto set approximations" (Year: 2018).
Miikkulainen et al, Mar. 3, 2017, "Evolving Deep Neural Networks" (Year: 2017).
Canadian Examination Report issued in App. No. CA3129731, dated Oct. 24, 2022, 4 pages.
Deychakiwsky Normalized Cross-Entropy—Deylemma, github.i io 2020 (Year: 2020).
Pan, L. et al., "A Classification-Based Surrogate-Assisted Evolutionary Algorithm for Expensive Many-objective Optimization", IEEE, https://ieeexplore.ieee.org/document/8281523, Feb. 1, 2019.
Robinet, V. et al., "Inducing High-Level Behaviors from Problem-Solving Traces Using Machine-Learning Tools", IEEE, https://ieeexplore.ieee.org/document/4287270, Aug. 13, 2007.
Canadian Examination Report issued in App. No. CA 3,131,688, dated Sep. 12, 2023, 4 pages.
Lopez Haimes et al., "MRMOGA: parallel evolutionary multi-objective optimization using multiple resolutions," In: Proceedings of IEEE Congress on Evolutionary Computation, 2294-2301, 2005.
Mahmoudpour et al., Diagnosis of Distributed Denial of Service Attacks using the Combination Method of Fuzzy Neural Network and Evolutionary Algorithm, Indian Journal of Science and Technology, vol. 8(28), DOI: 10.17485/ijst/2015/v8i28/81820, Oct. 2015; pp. 1-7 (Year: 2015).
Meyerson, Elliot, "Discovering Multi-Purpose Modules Through Deep Multitask Learning," Dissertation Presented to the Faculty of the Graduate School of the University of Texas at Austin, Dec. 2018, 275 pp.
Meyerson, et al., "Pseudo-Task Augmentation: From Deep Multitask Learning to Intratask Sharing and Back," arXiv:1803.04062, 10 pages, 2018.
Miikkulainen et al., Ascend by Evolv: AI-Based Massively Multivariate Conversion Rate Optimization, AI Magazine (2020). 16 pages.
Miikkulainen, Risto, et al., "Evolving Deep Neural Networks," Mar. 4, 2017, 8 pp.
Minsoo Kang, et al., "Towards Oracle Knowledge Distillation With Neural Architecture Search," arXiv: 1911.13019vl, Nov. 29, 2019, 9 pp.
Misra et al., "Cross-stitch networks for multi-task learning," in Proceedings of the IEEE Conference on Computer Vision and Pattern Recognition, pp. 3994-4003. 2016.
Moriarty etal., "Hierarchical Evolution of Neural Networks", IEEE (1998). (Year: 1998) 6 pages.
Moriarty, David E., et al., "Forming neural networks through efficient and adaptive coevolution," Evolutionary Computation 5.4, 28 pages, 1997.
N. Hansen, et al, "Adapting arbitrary normal mutation distributions in evolution strategies:The covariance matrix adaptation," in Proceedings of IEEE International Conference on Evolutionary Computation, pp. 312-317, IEEE, 1996.

(56) References Cited

OTHER PUBLICATIONS

N. Hansen, et al., "Evaluating the CMA evolution strategy on multimodal test functions," International Conference on Parallel Problem Solving from Nature, Springer, pp. 282-291, 2004.

Notice of Allowance for U.S. Appl. No. 13/358,381, dated Nov. 19, 2014, 5 pp.

Notice of Allowance for U.S. Appl. No. 13/540,507, dated Oct. 31, 2014, 9 pp.

O'Reilly et al., "EC-Star: A Massive-Scale, Hub and Spoke, Distributed Genetic Programming System", In: Riolo etal, Genetic Programming Theory and Practice X, Apr. 19, 2013, Genetic and Evolutionary Computation, pp. 73-85 (Year: 2013).

Oreski et al., Hybrid system with genetic algorithm and artificial neural networks and its application to retail credit risk assessment, Expert Systems with Applications 39 (2012); pp. 12605-12617 (Year: 2012).

Pantridge et al., Evolution of Layer Based Neural Networks: Preliminary Report, GECCO '16, pp. 1015-1022, Jul. 2016. (Year: 2016).

Paul Micaelli, et al., "Zero-Shot Knowledge Transfer via Adversarial Belief Matching," 33rd Conference on Neural Information Processing Systems, (NEURIPS 2019), Vancouver, CA, arXiv: 1905.09768v4, Nov. 25, 2019, 13 pp.

Pouya Bashivan, et al., "Teacher Guided Architecture Search," arXiv: 1808.01405v3, Sep. 6, 2019, 15pp.

R. Miikkulainen, J. Liang, E. Meyerson, et al., 2017, "Evolving Deep Neural Networks," CoRR, abs/1703.00548, Mar. 2017. 73 pages.

R. Poli, W. B. Langdon, N. F. McPhee, J. R. Koza, "Genetic programming: An introductory tutorial and a survey of techniques and applications", University of Essex, School of Computer Science and Electronic Engineering, Technical Report, (Oct. 2007), No. CES-475, ISSN 1744-8050, XP055038163.

Raphael Gontijo Lopes, et al., "Data-Free Knowledge Distillation for Deep Neural Networks," arXiv: 1710.07535v2, Nov. 23, 2017, 8 pp.

Rennie, Annealed dropout training of deep networks, 2014 IEEE Spoken Language Technology Workshop (SLT) 2014 (Year: 2014) 6 pages.

Risto Miikkulaiiien, "Evolving Multitask Neural Network Structure," The University of Texas at Austin and Sentient Technologies. Inc. Aug. 26, 2013, 22 pages.

Rosenbaum, et al., "Routing Networks: Adaptive Selection of Non-Linear Functions for Multi-Task Learning," In: Cornell University Library/Computer Science/Machine Learning, Dec. 31, 2017 [online] [retrieved on Mar. 15, 2019], Retrieved from the Internet: https://arxiv.org/abs/1711.01239v2. 16 pages.

Ruder,"An Overview of Multi-Task Learning in Deep Neural Networks," In: Cornell University Library /Computer Science/Machine Learning, Jun. 15, 2017 [online] [retrieved on Mar. 15, 2019], Retrieved from the Internet: https://arxrv.org/abs/1706.05098, 14 pages.

Salge, C., et al., "Empowerment—an Introduction," published in Guided Self-Organization: Inception, Chap 4, University of Hertfordshire, Copyright 2014, pp. 67-114.

Sanchez, "Advocating the Use of Imprecisely Observed Data in Genetic Fuzzy Systems", IEEE, 2007 (Year: 2007). 12 pages.

Santiago Gonzalez, "Loss Function Optimization Using Evolutionary Computation and Multivariate Function Approximators, Particularly Multivariate Taylor Expansions," 5 pp., Aug. 22, 2019.

Santiago Gonzalez, et al., "Improved Training Speed, Accuracy, and Data Utilization Through Loss Function Optimization," Version 1, arXiv: 1905.11528v1, dated May 27, 2019. 10 pages.

Santiago Gonzalez, et al., "Improved Training Speed, Accuracy, and Data Utilization Through Loss Function Optimization," Version 2, arXiv: 1905.11528v2, dated Feb. 10, 2020. 7 pages.

Santiago Gonzalez, et al., "Improved Training Speed, Accuracy, and Data Utilization Through Loss Function Optimization," Version 3, arXiv: 1905.11528v3, dated Apr. 27, 2020. 7 pages.

Scott, E. O., et. al., "Understanding Simple Asynchronous Evolutionary Algorithms," Jan. 17-20, 2015, 15 pp.

Secretan, J., et al., "Picbreeder: A Case Study in Collaborative Evolutionary Exploration of Design Space," Evolutionary Computation journal, MIT Press, Copyright 2011, 30 pages.

Shahrzad, et al., "Tackling the Boolean Multiplexer Function Using a Highly Distributed Genetic Programming System," in Genetic Programming Theory and Practice XII, 7 pp., 2015.

Shazeer et al., "Outrageously large neural networks: The sparsely-gated mixiure-of-experts layer," arXiv preprint arXiv:1701.08538 (2017), 19 pages.

Snoek, et al., "Scalable Bayesian Optimization Using Deep Neural Networks", 2015, 13 pages.

Stanley et al. "Evolving neural networks through augmenting topologies." Evolutionary computation 10.2, 29 pages (2002) (Year: 2002).

Stanley et al., Why greatness cannot be planned: the myth of the objective, Genet. Program Evolvable Mach.,m16:559-561, 2015.

Stanley, et al., "Why Greatness Cannot Be Planned: The Myth of the Objective," New York, NY, Springer (2015). 2 pages.

Stanley, Kenneth O., et al., "Real-Time Evolution of Neural Networks in the Nero Video Game," AAAI, vol. 6, 2006, 4 pp.

Supplementary European Search Report dated Oct. 12, 2012 in EP 10770288, 12 pages.

Supplementary European Search Report dated Oct. 9, 2012 in EP 107702871, 11 pages.

Timothy Hospedales, et al., "Meta-Learning in Neural Networks: A Survey," arXiv: 2004.05439vl, Apr. 11, 2020, 23 pp.

Torresen, "A Dynamic Fitness Function Applied to Improve the Generalisation when Evolving a Signal Processing Hardware Architecture," Proc. EvoWorkshops 2002, 267-299 (12 pp).

U.S. Appl. No. 13/184,307—Notice of Allowance dated Aug. 4, 2014, 9 pages.

U.S. Appl. No. 13/184,307—Office Action dated Oct. 21, 2013, 16 pages.

U.S. Appl. No. 14/595,991—Final Office Action dated Feb. 27, 2018, 25 pages.

U.S. Appl. No. 14/595,991—Response to Final Office Action dated Feb. 27, 2018, filed May 22, 2018, 32 pages.

Robinet et al ("Inducing High-Level Behaviors from Problem-Solving Traces Using Machine-Learning Tools" 2007) (Year: 2007).

Yao & Islam, 2008, "Evolving Artificial Neural Network Ensembles" (Year: 2008).

Oehmcke et al., "Knowledge Sharing for Population Based Neural Network Training," Springer (2018) (Year: 2018).

Ma et al., A multi-population differential evolution with best-random mutation strategy for large-scale global optimization (Jan. 2020) (Year: 2020).

H. Li, et al., "Visualizing the loss landscape of neural nets," Advances in Neural Information Processing Systems 31, pp. 6389-6399 (Curran Associates, Inc., 2018), arXiv:1712.09913v3, Nov. 7, 2018.

Haitong Li, "Exploring Knowledge Distillation of Deep Neural Networks for Efficient Hardware Solutions," CS 230 Final Report, Department of Electrical Engineering, Stanford, CA, 6 pp., 2018.

Hansen, et al., "Completely derandomized self-adaptation in evolution strategies," Evolutionary Computation, vol. 9, No. 2, pp. 159-195, 2001.

Hanting Chen, et al., "Data-Free Learning of Student Networks," arXiv: 1904.01186v4, Dec. 31, 2019, 9 pp.

Hodjat et al., "Maintenance of a Long Running Distributed Genetic Programming System for Solving Problems Requiring Big Data",In: Riolo et al., Genetic Programming Theory and Practice X, Mar. 10, 2014, Genetic and Evolutionary Computation, pp. 65-83 (Year: 2014).

Hodjat et. al., "nPool: Massively Distributed Simultaneous Evolution and Cross-Validation in EC-Star", ppt at GPTP May 2015, 16 pages.

Hornby, "ALPS: The Age-Layered Population Structure for Reducing the Problem of Premature Convergence," GECCO '06, Seattle, WA, Jul. 2006, 8 pp.

International Preliminary Report on Patentability for PCT App. PCT/US2019/061198, dated Nov. 18, 2020, 24 pp.

(56) References Cited

OTHER PUBLICATIONS

International Search Report and Written Opinion for Application No. PCT/US2018/064520, dated Mar. 4, 2019. 8 pages.
International Search Report and Written Opinion for PCT App. No. PCT/US19/61198, dated Mar. 11, 2020, 15 pp.
International Search Report and Written Opinion for PCT Application No. PCT/US18/64428, dated Mar. 26, 2019, 12 pp.
International Search Report and Written Opinion for PCT Application No. PCT/US18/65472, dated Mar. 27, 2019, 8 pp.
International Search Report and Written Opinion for PCT Application No. PCT/US18/66610, dated Apr. 15, 2019, 8 pp.
International Search Report and Written Opinion for PCT Application No. PCT/US2019/017175, dated Jun. 5, 2019, 10 pp.
International Search Report mailed Jun. 29, 2010 in PCT/US 10/32841, 3 pages.
Ishibuchi, "Three-objective genetics-based machine learning for linguistic rule extraction", IEEE, 2005 (Year: 2005). 25 pages.
J. Z. Liang, et al., "Evolutionary Architecture Search for Deep Multitask Networks," GECCO, 2018.
J.T. Barron, "A General and Adaptive Robust Loss Function," arXiv: 1701.03077, 2018, 19 pages.
Jaemin Yoo, et al., "Knowledge Extraction With No Observable Data," 33rd Conference on Neural Information Processing Systems (NeurIPS 2019), Vancouver, Canada, 2019, 10 pp.
James Bradbury, et al., "Quasi-Recurrent Neural Networks," arXiv:1611.01576v2, Nov. 21, 2016, 11 pp.; Retrieved from the Internet: https//arxiv.org/pdf/1611.01576.pdf?fbclid=1wAR3hreOvBGmJZe54-631X49XedcbsQoDYIRu87BcCHEBf_vMKF8FDKK_7Nw.
Jason Liang, et al., "Evolutionary Neural AutoML for Deep Learning," GECCO '19, Jul. 13-17, 2019, Prague, Czech Republic (https://arxiv.org/pdf/1902.06827.pdf).
Jee-weon Jung, et al, "Distilling the Knowledge of Specialist Deep Neural Networks in Acoustic Scene Classification," Detection and Classification of Acoustic Scenes and Events 2019, New York, New York, Oct. 25-26, 2019, 5 pp.
Ji Wang, et al., "Private Model Compression via Knowledge Distillation," arXiv: 1811.05072vl, Nov. 13, 2018, 9 pp.
JP 2010-533295—Office Action, dated Apr. 16, 2013, 3 pp. (English translation). 3 pages.
JP 2012-508660—Office Action dated Apr. 1, 2014, 8 pages.
JP 2012-508663—Office Action dated Apr. 1, 2014, 6 pages.
Juille, H., "Evolution of Non-Deterministic Incremental Algorithms as a New Approach for Search in State Spaces, Proc. 6th Int'l. Conf. on Genetic Algorithms," 1995 8 pp.
Jul. 27, 2012 Final Office Action in U.S. Appl. No. 12/267,287, 14 pp.
Julian G. Zilly, Rupesh Kumar Srivastava, Jan ICoutnik, and Jurgen Schniidhuber, "Recurrent Hiehwav Networks." CORR abs/1607.03474. 2016 (Arxiv: 1607.03474} 13 pages.
Jun. 16, 2011 Written Opinion from Singapore Patent Office in related application SG 201003127—68 pp.
Jun. 16, 2011 Written Opinion from Singapore Patent Office in related application SG 201093127-6, 9 pp.
K. Janocha and W. M. Czarnecki, "On Loss Functions for Deep Neural Networks in Classification," arXiv: 1702.05659, 10 pages, 2017.
Kang, Zhuoliang, et al., "Learning With Whom to Share in Multi-Task Feature Learning," Proceedings of the 28th International Conference on Machine Learning, Bellevue, WA, USA, 2011, 8 pp.
Kenneth O. Stanley and Risto Miikkulainen, "Evolving Neural Networks Through Augmenting Topologies," Evolutionary Computation, 10(2):99-127, 2002.
Kipfer et al., "UberFlow: A GPU-Based Particle Engine," Computer Graphics and Visualization, The Eurographics Association, Copyright 2004, 9 pages.
Krcah, P., et al., "Combination of Novelty Search and Fitness-Based Search Applied to Robot Body-Brain Co-Evolution," Charles University, Prague Czech Republic, in Proceedings of the 13th Czech-Japan Seminar on Data Analysis and Decision Making in Service Science, 2010, 6 pages.
Krizhevsky, Alex, et al., "ImageNet Classification with Deep Convolutional Neural Networks", Advances in Neural Information Processing Systems 25 (NIPS 2012), Lake Tahoe, Nevada, Dec. 3-6, 2012, 9 pp.
Kwedlo, "Learning Decision Rules Using a Distributed Evolutionary Algorithm", 2002 (Year: 2002). 10 pages.
Lahsasna, "Design of a Fuzzy-based Decision Support System for Coronary Heart Disease Diagnosis", (Year: 2012). 14 pages.
Lee, Chi-Ho, et al., "Evolutionary ordered neural network with a linked-list encoding scheme," Proceedings of IEEE International Conference on Evolutionary Computation, IEEE, 5 pages, 1996.
Lehman et al., "Evolving a Diversity of Creatures through Novelty Search and Local Competition," Proceedings of the Genetic and Evolutionary Computation Conference, ACM, New York, NY, 2011, 8 pages.
Lehman et al., "Abandoning Objectives: Evolution through the Search for Novelty Alone," Evolutionary Computation journal, MIT Press, Copyright 2011, pp. 189-223.
Lehman et al., "Efficiently Evolving Programs through the Search for Novelty," Proceedings of the Genetic and Evolutionary Computation Conference, ACM, New York NY, Copyright 2010, 8 pages.
Lehman et al., "Extinction Events Can Accelerate Evolution," PLOS One, journal.pone.0132886, Aug. 12, 2015, 16 pages.
Lehman et al., "Overcoming Deception in Evolution of Cognitive Behaviors," University of Texas at Austin, ACM, Jul. 12-16, 2014, 8 pages.
Lehman et al., "Revising the Evolutionary Computation Abstraction: Minimal Criteria Novelty Search," Proceedings of the Genetic and Evolutionary Computation Conference, ACM, Copyright 2010, 8 pages.
Lehman, Joel, et al., "Exploiting Open-Endedness to Solve Problems Through the Search for Novelty," ALIFE, 8 pages, 2008.
Leon, C. et al., 'Parallel hypervolume-guided hyperheuristic for adapting the multi-objective evolutionary island model', NICSO 2008, Studies in Computational Intelligence, Nov. 12, 2008, vol. 236pp. 261-272.
Liang, et al, "Population-Based Training for Loss Function Optimization," 10 pages, arXiv:2002.04225vl (Feb. 11, 2020).
Lin Wang, et al., "Knowledge Distillation and Student-Teacher Learning for Visual Intelligence: A Review and New Outlooks," Journal of Latex Class Files, vol. 14, No. 8, Apr. 2020, 38 pp., arXiv: 2004/05937v3, May 4, 2020.
Wissner-Gross, et al., "Causal Entropic Forces," Physical Review Letters, PRL 110.168702, American Physical Society, Apr. 19, 2013, 5 pages.
Xu, et al., "Inference of Genetic Regulatory Networks With Recurrent Neural Network Models Using Particle Swarm Optimization," Missouri University of Science and Technology, Oct. 2017, 36 pages, [retrieved on Feb. 14, 2019], Retrieved from the Internet: http://scholarsmine.mst.edu/cgi/viewcontent.cgi?article=1751&context=ele_comeng_facwork.
Yang et al., "Deep multi-task representation learning: A tensor factorisation approach," arXiv preprint arXiv:1605.06391 (2016), 12 pages.
Yang Fan, et al., "Learning to Teach," ICLR 2018, arXiv: 1805.03643vl, May 9, 2018, 16 pp.
Yin et al., "ABCNN: Attention-Based Convolutional Neural Network for Modeling Sentence Pairs", Transactions of the Association for Computational Linguistics, (Dec. 16, 2015), vol. 4, pp. 259-272, XP081355040.
Zhang, et al., "Evolutionary Computation Meets Machine Learning: A Survey," IEEE Computational Intelligence Magazine, vol. 6, No. 4, DOI 10.1109/MCI.2011.942584, 2011.
Zhang, Loy, "Facial Landmark Detection by Deep Multi-Task Learning," in Proceedings of ECCV'14, 2014, 15 pages.
U.S. Appl. No. 14/595,991—Response to Final Office Action dated Feb. 27, 2018, filed Jul. 27, 2018, 41 pages.
U.S. Appl. No. 13/184,307—Response dated Jan. 22, 2014, 19 pages.
U.S. Appl. No. 13/184,307—Response dated Jun. 23, 2014, 32 pages.
U.S. Appl. No. 13/358,381—Response dated Oct. 3, 2014, 21 pages.

(56) References Cited

OTHER PUBLICATIONS

U.S. Appl. No. 13/358,381—Amendment After Allowance filed Feb. 13, 2015, 20 pages.
U.S. Appl. No. 13/540,507—Response filed Oct. 15, 2014, 20 pages.
U.S. Appl. No. 13/895,238—Office Action dated Jan. 2, 2014, 17 pages.
U.S. Appl. No. 13/943,630—Amendment After Allowance dated Mar. 15, 2016, 16 pages.
U.S. Appl. No. 13/943,630—Notice of Allowance dated Jan. 21, 2016, 28 pages.
U.S. Appl. No. 13/943,630—Notice of Allowance dated May 19, 2016, 2 pages.
U.S. Appl. No. 13/943,630—Office Action dated May 27, 2015, 42 pages.
U.S. Appl. No. 13/943,630—Response to Office Action dated May 27, 2015 filed Sep. 23, 2015, 8 pages.
U.S. Appl. No. 13/945,630—Amendmend After Allowance dated Dec. 9, 2015, 7 pages.
U.S. Appl. No. 13/945,630—Final Office Action dated Aug. 4, 2015, 22 pages.
U.S. Appl. No. 13/945,630—Notice of Allowance dated Nov. 18, 2015, 8 pages.
U.S. Appl. No. 13/945,630—Office Action dated Mar. 12, 2015, 18 pages.
U.S. Appl. No. 13/945,630—Resonse to Office Action dated Mar. 12, 2015 filed Jul. 13, 2015, 9 pages.
U.S. Appl. No. 13/945,630—Response filed Nov. 4, 2015, 12 pp.
U.S. Appl. No. 14/014,063—Office Action dated May 7, 2014, 19 pages.
U.S. Appl. No. 14/539,908—Notice of Allowance dated Mar. 17, 2016, 15 pages.
U.S. Appl. No. 14/539,908—Office Action dated Oct. 1, 2015, 33 pages.
U.S. Appl. No. 14/539,908—Response filed Feb. 1, 2016, 18 pp.
U.S. Appl. No. 14/595,991—Office Action, dated Feb. 27, 2018, 19 pp.
U.S. Appl. No. 14/595,991—Response to Office Action dated May 10, 2017, filed Nov. 10, 2017, 29 pages.
U.S. Appl. No. 15/794,905, titled Evolution of Deep Neural Network Structures, 46 pages, filed Oct. 26, 2017.
U.S. Appl. No. 15/794,913 titled "Cooperative Evolution of Deep Neural Network Structures," filed Oct. 26, 2017.
U.S. Appl. No. 15/915,028, titled "Asynchronous Evaluation Strategy for Evolution of Deep Neural Networks," filed Mar. 3, 2018.
U.S. Appl. No. 62/468,224, titled "Asynchronous Evaluation Strategy for Evolution of Deep Neural Networks," filed Mar. 7, 2017.
U.S. Appl. No. 62/598,409, titled "Evolving Multitask Neural Network Structure," filed Dec. 13, 2017.
U.S. Appl. No. 62/627,161, titled "From Nodes to Networks: Evolving Recurrent Neural Networks," filed Feb. 6, 2018.
U.S. Appl. No. 62/627,658, titled "From Nodes to Networks: Evolving Recurrent Neural Networks," filed Feb. 7, 2018.
Unpublished Article, Modular Universal Reparameterization: Deep Multi-Task Learning Across Diverse Domains, 10 pp.
U.S. Appl. No. 13/184,307—Office Action dated Mar. 21, 2014, 38 pages.
U.S. Appl. No. 13/358,381—Office Action dated Jul. 8, 2014, 30 pages.
U.S. Appl. No. 13/540,507—Office Action dated Sep. 9, 2014, 25 pages.
U.S. Appl. No. 13/945,630—Response to Final Office Action dated Aug. 4, 2015 filed Nov. 4, 2015, 12 pages.
U.S. Appl. No. 14/539,908—Response to Office Action dated Oct. 1, 2015 filed Feb. 1, 2016, 18 pages.
U.S. Appl. No. 14/595,991—Office Action dated May 10, 2017, 32 pages.
U.S. Appl. No. 15/794,905—Non Provisional Application filed Oct. 26, 2017, 60 pages.
U.S. Appl. No. 15/794,913—Non-Provisional Application filed Oct. 28, 2017, 73 pages.
Utech, J., et al., "An evolutionary algorithm for drawing directed graphs," Proc. of the Int. Conf. on Imaging Science, Systems and Technology, 8 pages, 1998.
Valsalam, V.K., et al., "Using Symmetry and Evolutionary Search to Minimize Sorting Networks," Journal of Machine Learning Research 14, The University of Texas at Austin, Department of Computer Science, Copyright Sep. 2013, pp. 303-331.
Alois Pourchot et. al. , "CEM-RL: Combining evolutionary and gradient-based methods for policy search", arXiv preprint arXiv:1810.01222v3, Oct. 2, 2018. 19 pages.
Open Ai: "Deep Deterministic Policy Gradient—Spinning Up documentation", Nov. 12, 2018, URL: https://web.archive.org/web/20181112044227/https://spinningup.openai.com/en/latest/algorithms/ddpg.html [retrieved on Feb. 15, 2023], 7 pages.
Tobias Peter: "Using Deep Learning as a surrogate model in Multi-objective Evolutionary Algorithms", Jan. 1, 2018, URL:https://www.ci.ovgu.de/is_media/Master+und+Bachelor_Arbeiten/MasterThesis_TobiasPeter-download-p-4614.pdf [retrieved on Feb. 14, 2023], 115 pages.
Extended European Search Report issued in App. No. EP20778409.1 on Feb. 27, 2023, 11 pages.
Extended EPO Search Report, App. No. 19878418.3-1203/3942483 PCT/US2019061198, May 27, 2022.
Elsken Thomas et al., Efficient Multi-Objective Neural Architecture Search via Lamarckian Evolution, ICLR 2019, Feb. 26, 2019 (URL: https://arxiv.org/pdf/1804.09081.pdf).
Lu Zhichao et al., NSGA-NET neural architecture search using multi-objective genetic algorithm, Proceedings of the Genetic and Evolutionary Computation Conference, ACMPUB27, NY, NY, Jul. 13, 2019.
Yuan, F., Shou, L., Pei, J., Lin, W., Gong, M., Fu, Y., & Jiang, D. Reinforced MultiTeacher Selection for Knowledge Distillation. Proceedings of the AAAI Conference on Artificial Intelligence, 35(16), pp. 14284-14291. May 18 (Year: 2021).
Grushka-Cohen, A framework for optimizing COVID-19 testing policy using a Multi Armed Bandit approach, pp. 1-9, Jul. (Year: 2020).
Lu, Evolutionary optimization with hierarchical surrogates, Swarm and Evolutionary Computation 47. pp. 21-32 (Year: 2019).
Rowland, Model selection methodology in supervised learning with evolutionary computation, BioSystems 72, pp. 187-196. (Year: 2003).

\* cited by examiner

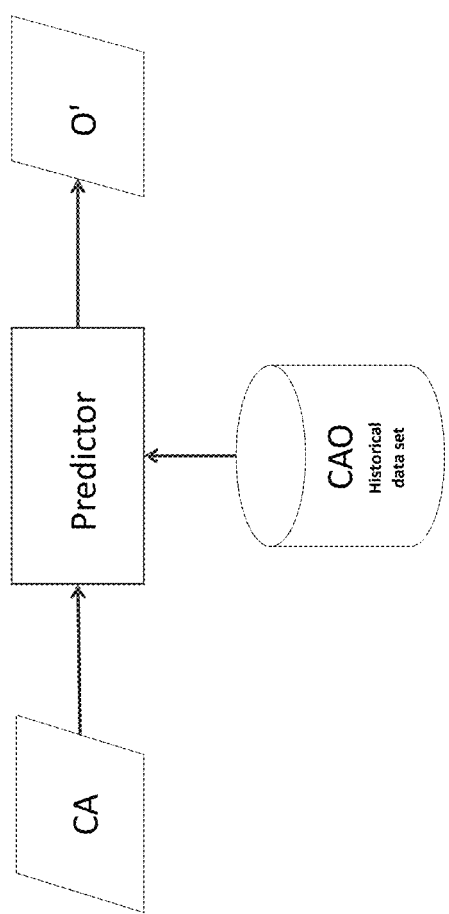

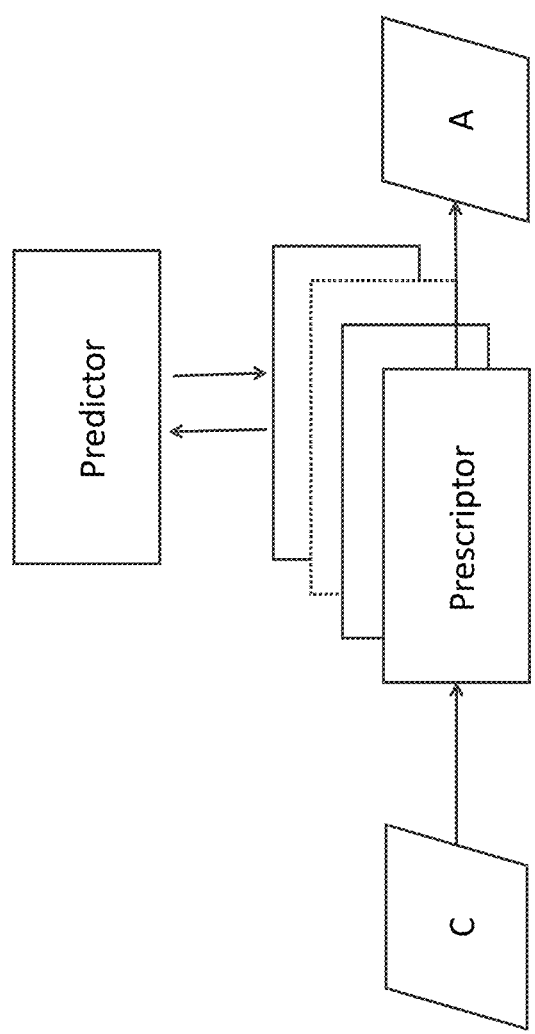

| NPI name | Level 0 | Level 1 | Level 2 | Level 3 | Level 4 |
|---|---|---|---|---|---|
| C1_School closing | no measures | recommend closing | require closing (only some levels or categories, e.g. just high school, or just public schools) | require closing all levels | |
| C2_Workplace closing | no measures | recommend closing (or recommend work from home) | require closing (or work from home) for some sectors or categories of workers | require closing (or work from home) for all-but-essential workplaces (e.g. grocery stores, doctors) | |
| C3_Cancel public events | no measures | recommend cancelling | require cancelling | | |
| C4_Restrictions on gatherings | no restrictions | restrictions on very large gatherings (the limit is above 1000 people) | restrictions on gatherings between 101-1000 people | restrictions on gatherings between 11-100 people | restrictions on gatherings of 10 people or less |
| C5_Close public transport | no measures | recommend closing (or significantly reduce volume/ route/means of transport available) | require closing (or prohibit most citizens from using it) | | |
| C6_Stay at home requirements | no measures | recommend not leaving house | require not leaving house with exceptions for daily exercise, grocery shopping, and "essential" trips | require not leaving house with minimal exceptions (e.g. allowed to leave once a week, or only one person can leave at a time, etc.) | |
| C7_Restrictions on internal movement | no measures | recommend not to travel between regions/cities | internal movement restrictions in place | | |
| C8_International travel controls | no restrictions | screening arrivals | quarantine arrivals from some or all regions | ban arrivals from some regions | ban on all regions or total border closure |

FIGURE 3

AI BASED OPTIMIZED DECISION MAKING FOR EPIDEMIOLOGICAL MODELING

CROSS-REFERENCE TO RELATED APPLICATIONS

The present application claims the benefit of priority to U.S. Provisional Patent Application No. 63/049,370, "AI BASED OPTIMIZED DECISION MAKING FOR EPIDEMIOLOGICAL MODELING" which was filed on Jul. 8, 2020 and which is incorporated herein by reference in its entirety.

Cross-reference is also made to U.S. patent application Ser. No. 16/831,550 entitled "PROCESS AND SYSTEM INCLUDING AN OPTIMIZATION ENGINE WITH EVOLUTIONARY SURROGATE-ASSISTED PRESCRIPTIONS" which was filed on Mar. 26, 2020; U.S. patent application Ser. No. 16/902,013 entitled "PROCESS AND SYSTEM INCLUDING EXPLAINABLE PRESCRIPTIONS THROUGH SURROGATE-ASSISTED EVOLUTION" which was filed on Jun. 15, 2020; and U.S. patent application Ser. No. 17/209,623 entitled "FRAMEWORK FOR INTERACTIVE EXPLORATION, EVALUATION, AND IMPROVEMENT OF AI-GENERATED SOLUTIONS" which was filed on Mar. 23, 2021, each of which is incorporated herein by reference in their entireties.

The following publication is also incorporated herein by reference: Miikkulainen et al., "From Prediction to Prescription: Evolutionary Optimization of Non-Pharmaceutical Interventions in the COVID-19 Pandemic," IEEE TRANSACTIONS ON EVOLUTIONARY COMPUTATION, VOL. 25, NO. 2, April 2021.

Additionally, one skilled in the art appreciates the scope of the existing art which is assumed to be part of the present disclosure for purposes of supporting various concepts underlying the embodiments described herein. By way of particular example only, prior publications, including academic papers, patents and published patent applications listing one or more of the inventors herein are considered to be within the skill of the art and constitute supporting documentation for the embodiments discussed herein.

COMPUTER PROGRAM LISTING

A Computer Program Listing is included in an Appendix to the present specification. The Appendix is provided on a compact disc and the Computer Program Listing thereon is incorporated herein by reference in its entirety. The Computer Program Listing includes the following file which was created on Jun. 11, 2021 and included on compact disc:
27.7 kb "xprize_predictor.py.txt"

FIELD OF INVENTION

The subject matter described herein, in general, relates to AI based optimized decision making for epidemiological modeling, and, in particular, relates to ESP decision optimization approach for determining effective intervention strategies, automatically implementable at different stages of pandemic.

BACKGROUND OF INVENTION

COVID-19 crisis is unprecedented in modern times, and caught the world largely unprepared. Since there is little experience and guidance, authorities have been responding in a variety of ways. Many different non-pharmaceutical interventions (NPIs) have been implemented at different stages of the pandemic and in different contexts. On the other hand, compared to past pandemics, for the first time almost real-time data is collected about these interventions, their economic impact, and the spread of the disease. These two factors create an excellent opportunity for computational modeling and machine learning.

Most of the modeling efforts so far have been based on traditional epidemiological methods, such as compartmental models. Such models can be used to predict the spread of the disease, assuming a few parameters, such as the basic reproduction number $R_0$ can be estimated accurately. New ideas have also emerged, including using cell-phone data to measure social distancing. These models have been extended with NPIs by modifying the transmission rates: each NPI is assumed to reduce the transmission rate by a certain amount. Such models have received a lot of attention. And in this unprecedented situation, they are our only source of support for making informed decisions on how to reduce and contain the spread of the disease.

However, epidemiological models are far from perfect. Much about how the disease is transmitted, how prevalent it is in the population, how many people are immune, and how strong the immunity is, is unknown, and it is difficult to parameterize the models accurately. Similarly, the effects of NPIs are unpredictable in that their effects vary based on the cultural and economic environment and the stage of the pandemic, and above all, they interact in nonlinear ways. To overcome the uncertainty, data is crucial. Model parameters can be estimated more accurately by fitting them to existing data. With enough data, however, it is also possible to use machine learning simply to model the data with few assumptions. The unknown epidemiological, cultural, and economic parameters and interactions are expressed in the time series of infections and NPIs. Machine learning can then be used to construct a model, such as a recurrent neural network (RNN), that predicts the outcomes accurately without having to understand precisely how they emerge.

One popular epidemiological model-compartmental SIR metapopulation model enables random mixing between individuals within population subgroups only. It requires several assumptions about the population, culture, and environment, depends on several parameters that are difficult to set accurately, and cannot take into account many possible nonlinear and dynamic interactions between the non-pharmaceuticals interventions (NPIs), and in the population. Most forecast approaches use curve fitting and ensembles of mechanistic SIR models with different parameter assumptions. However, social distancing and NPIs are usually not represented directly, but instead are approximated as changes in transmission rates.

On the other hand, other models focusing on evolutionary and adaptive networks attempting to overcome above limitations of modeling the dynamics of social links, require appropriate calibration of parameters, which is difficult to do with the limited available data. Further, these models rely on extensive computational powers to simulate effects of NPIs. They are usually met with data collection challenges and issues related to sampling of real networks due to limited resources and data availability, in addition to requiring significant computing resources and sophisticated parallelization algorithms. While these known models are predictive, these models do not make recommendations, or prescriptions, of what NPIs would be most effective. What is missing is an extension of models from prediction to prescription. That is, given that we can predict how the NPIs affect the pandemic, how we can also automatically discover effective NPI strategies. The technology required for this step is different from standard machine learning. The goal is not to model and predict processes for which data already exists, but to create new solutions that may have never existed before. In other words, it requires extending AI from imitation to creativity.

There is a need in the art for an automated, less costly, dynamic method for adaptive decision-making in accurate epidemiological modeling by automatic discovery effective of NPI strategies from limited available data.

SUMMARY OF THE EMBODIMENTS

In a first exemplary embodiment, a system for automatic discovery of non-pharmaceutical intervention (NPI) strategies to optimize one or more objectives related to an epidemiological event, includes: a predictor model, $P_d(C, A)=O$, implemented on a processor, the predictor model being configured to receive input data, the input data including context information (C) and actions (A) performed in a given context, and predict an outcome (O) based on the input data, wherein the outcome includes data for the one or more objectives; a prescriptor model, $P_s(C)=A$, implemented on a processor, the prescriptor model being configured to receive context information as input data, wherein the context information includes epidemiological event data; and output actions that optimize the one or more objectives as outcomes corresponding to the context, wherein the output actions include changes to the implementation of one more non-pharmaceutical interventions (NPIs); wherein the prescriptor model is evolved over multiple generations using the predictor model as a surrogate.

In a second exemplary embodiment, a computer-implemented process for automatic discovery of non-pharmaceutical intervention (NPI) strategies to optimize one or more objectives related to an epidemiological event, includes: training a predictor model, $P_d(C, A)=O$, implemented on a processor, the predictor model being configured to receive input training data, the input historical training data sets (C, A, O) including context information (C), actions (A) performed in a given context, and outcomes (O) resulting from action performed in the given context; evolving a prescriptor model, $P_s(C)=A$, implemented on a processor, wherein the prescriptor model is evolved over multiple generations using the trained predictor model as a surrogate, the prescriptor model being configured to receive context information as input data, wherein the context information includes epidemiological event data; and output actions that optimize the one or more objectives as outcomes corresponding to the received context information, wherein the output actions include changes to the implementation of one more non-pharmaceutical interventions (NPIs).

In a third exemplary embodiment, at least one computer-readable medium storing instructions that, when executed by a computer, perform a process for automatic discovery of non-pharmaceutical intervention (NPI) strategies to optimize one or more objectives related to an epidemiological event, including: training a predictor model, $P_d(C, A)=O$, the predictor model being configured to receive input training data, the input historical training data sets (C, A, O) including context information (C), actions (A) performed in a given context, and outcomes (O) resulting from action performed in the given context; evolving a prescriptor model, $P_s(C)=A$, wherein the prescriptor model is evolved over multiple generations using the trained predictor model as a surrogate, the prescriptor model being configured to receive context information as input data, wherein the context information includes epidemiological event data; and output actions that optimize the one or more objectives as outcomes corresponding to the received context information, wherein the output actions include changes to the implementation of one more non-pharmaceutical interventions (NPIs).

In a fourth exemplary embodiment, a computer-implemented process for automatic discovery of one or more strategies to optimize one or more objectives related to an event in the time series domain, includes: training a predictor model, $P_d(C, A)=O$, implemented on a processor, the predictor model being configured to receive input training data, the input historical training data sets (C, A, O) including context information (C), actions (A) performed in a given context, and outcomes (O) resulting from action performed in the given context; evolving a prescriptor model, $P_s(C)=A$, implemented on a processor, wherein the prescriptor model is evolved over multiple generations using the trained predictor model as a surrogate, the prescriptor model being configured to receive context information as input data, wherein the context information includes time series data; and output actions that optimize the one or more objectives as outcomes corresponding to the received context information.

BRIEF DESCRIPTION OF FIGURES

FIGS. 2a, 2b, 2c illustrate construction of Predictor and Prescriptor models, in accordance with a preferred embodiment;

FIG. 3 provides details for the eight kinds of non-pharmaceuticals interventions (NPIs) and range of stringency identified in the dataset used with a preferred embodiment;

DETAILED DESCRIPTION OF THE EMBODIMENTS

In describing the preferred and alternate embodiments of the present disclosure, specific terminology is employed for the sake of clarity. The disclosure, however, is not intended to be limited to the specific terminology so selected, and it is to be understood that each specific element includes all technical equivalents that operate in a similar manner to accomplish similar functions. The disclosed embodiments are merely exemplary methods of the invention, which may be embodied in various forms Generally, the embodiments herein describe an Evolutionary Surrogate-assisted Prescription (ESP)-based optimization approach for predicting how a pandemic may unfold in the future within various parts of world. The data-driven modeling approach is adopted to extend the model from prediction to prescription by predicting how the non-pharmaceutical interventions (NPIs) affect the pandemic, and subsequently automatically discovering effective NPI strategies. Machine learning may be used to construct a model, such as a recurrent neural network, that accurately predicts the outcomes without having to understand precisely how they emerge.

Figure 1:
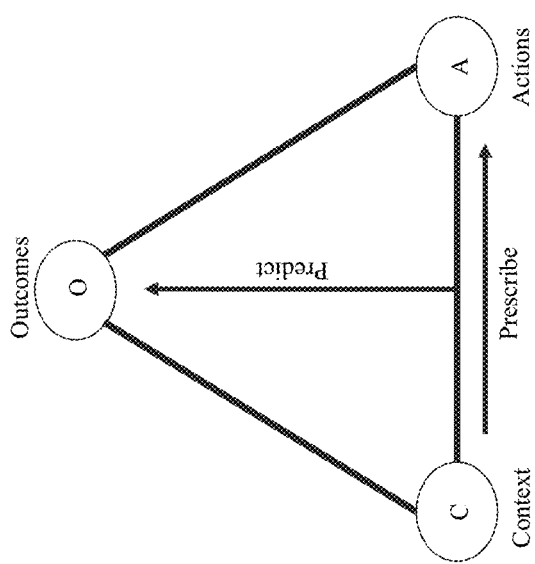
FIG. 1 illustrates elements of ESP decision optimization system, in accordance with a preferred embodiment.

In accordance with a preferred embodiment of a present disclosure, evolutionary surrogate-assisted prescription (ESP), a technique that combines evolutionary search with surrogate modeling (shown in FIG. 1), is adopted. ESP is a continuous black-box optimization process for adaptive decision-making. In ESP, a model of the problem domain is used as a surrogate for the problem itself. The ESP approach is summarized below and more specifically discussed in co-pending U.S. patent application Ser. No. 16/831,550 entitled "PROCESS AND SYSTEM INCLUDING AN OPTIMIZATION ENGINE WITH EVOLUTIONARY SURROGATE-ASSISTED PRESCRIPTIONS," which is incorporated herein by reference in its entirety.

In accordance with a general embodiment, in ESP, a first predictive model (Predictor ($P_d$)) is formed through standard machine learning techniques, such as neural networks. Given actions (A) taken in a given context (C) (such as NPIs at a given stage of the pandemic), it predicts what the outcomes (O) would be (such as infections, deaths, and economic cost). A second prescriptive model (Prescriptor ($P_s$)), e.g., another neural network, is then formed to implement an optimal decision strategy, i.e. what actions should be taken in each context. Such optimal actions are not known, as the Prescriptor cannot be trained with standard supervised learning. However, it can be evolved i.e. discovered through population-based search. Because it is often impossible or prohibitively costly to evaluate each candidate strategy in the real world, the predictor model is used as a surrogate. The Prescriptor takes a context as its input, and outputs actions that would optimize outcomes in that context. In order to develop the Prescriptor, the Predictor is used as the surrogate.

More formally, given a set of possible contexts C' and possible actions A', a decision policy D returns a set of actions (A) to be performed in each context (C):

$$D(C)=A, \quad (1)$$

where C∈C' and A∈A'. As shown in FIG. 2(a), the Predictor takes, as its input, context information (C), as well as actions (A) performed in that context, along with historical C, A, O data sets. The output of the Predictor is the resulting outcomes when the given actions are applied in the given context. The Predictor is therefore defined as $$P_d(C,A)=O, \quad (2)$$

such that $\Sigma j\ L(Oj, Oj')$ across all dimensions j of O is minimized. The function L can be any of the usual loss functions used in machine learning, such as cross-entropy or mean-squared-error, and the model $P_d$ itself can be any supervised machine learning model such as a neural network or a random forest.

As shown in FIG. 2(b), the Prescriptor takes a given context as input, and outputs a set of actions:

$$P_s(C)=A, \quad (3)$$

such that $\Sigma i, j\ Oj'(Ci, Ai)$ over all possible contexts i is maximized. It thus approximates the optimal decision policy for the problem. Note that the optimal actions A are not known, and must therefore be found through search.

In the case of NPI optimization problem, context C consists of information regarding a region. This might include data on the number of available ICU beds, population distribution, time since the first case of the disease, and fatality rate. Actions (A) in this case specify whether the different possible NPIs are implemented within that region. The outcomes (O) for each decision measure the number of cases and fatalities within predetermined time of the decision, and the cost of each NPI.

The ESP algorithm then operates as an outer loop in a continuous learning and optimization process that constructs the predictor and prescriptor models as follows (FIG. 2c):

(1) Train a Predictor based on historical training data; (S1)
(2) Evolve Prescriptors with the Predictor as the surrogate; (S2)
(3) Apply the best Prescriptor in the real world; (S3)
(4) Collect the new data and add to the training set; (S4)
(5) Repeat until convergence. (S5)

In the case of the NPI optimization, there is currently no step S3 since the system is not yet incorporated into decision making. However, any NPIs implemented in the real world, whether similar or dissimilar to ESP's prescriptions, will similarly result in new training data. As usual in evolutionary search, the process terminates when a satisfactory level of outcomes is reached, or no more progress can be made, or the system iterates indefinitely, continuously adapting to changes in the real world (e.g., adapting to the advent of vaccines or antiviral drugs). Note that not all data needs to be accumulated for training each iteration. In domains where the underlying relationships between variables might change over time, it might be advisable to selectively ignore samples from the older data as more data is added to the training set in S4. It is thus possible to bias the training set towards more recent experiences.

The Predictor model is built by modeling a (C, A, O) dataset. The choice of algorithm depends on the domain, i.e., how much data there is, whether it is continuous or discrete, structured or unstructured. Random forests, symbolic regression, and neural networks have been used successfully in this role in the past. In some cases, such as NPI optimization, an ensemble of data-driven and simulation models may be useful, in order to capture expected or fine-grained behavior that might not yet have been reflected in the data.

The Prescriptor model is built using neuroevolution: neural networks because they can express complex nonlinear mappings naturally, and evolution because it is an efficient way to discover such mappings and a natural way to optimize multiple objectives. Because it is evolved with the Predictor, the Prescriptor is not restricted by a finite training dataset, or limited opportunities to evaluate in the real world. Instead, the Predictor serves as a fitness function, and it can be queried frequently and efficiently. In a multi-objective setting, ESP produces multiple Prescriptors, selected from the Pareto front of the multiobjective neuroevolution run. The Prescriptor is the novel aspect of ESP: it makes it possible to discover effective solutions that do not already exist, even solutions that might be overlooked by human decision makers.

In the NPI optimization task of the exemplary embodiment, ESP is built to prescribe the NPIs for the current day such that the number of cases and cost that would result in the next two weeks is optimized. For the exemplary embodiment, the initial NPI dataset is based on datasets from Oxford University's Blavatnik School of Government which created a comprehensive representation of the different NPIs, characterized by type and different stringency, and encoded historical data in over 180 countries into this format since the beginning of the pandemic. The data also includes cases and deaths, and is updated continuously during the course of the pandemic. Such a common encoding is crucial for data-driven modeling to work. The NPI implementations at different countries must have significant overlap so that common principles can be learned. FIG. 3 provides details for the eight kinds of NPIs and range of stringency identified in the dataset. For training the model, data-depicting number of cases, deaths and the NPIs for various countries is used as a feed. Data being very noisy is curated for various informalities before being used to develop a predictive model using machine-learning techniques. In one exemplary embodiment, deep learning approaches can be made in this process to sequence processing, in particular recurrent neural networks.

Next, in accordance with one general embodiment, design of a learned predictor is discussed. Accordingly, at first a training target or factor is chosen to be predicted from data collected from various, disparate sources. Unreasonably high noise in daily data is smoothed based on a moving average of new cases. Now, the trainable function implementing predicted factor is made a function of (1) NPIs enacted over previous days, and (2) the underlying state of the pandemic distinct from the enacted NPIs. However, in contrast to epidemiological models that make predictions based on today's state only, the data driven model predicts based on data from preceding weeks.

To help the model generalize with a relatively small amount of training data, the model is made more tractable by decomposing trainable function with respect to its inputs/factors. In one working embodiment, these factors can be viewed as 1) effect of social distancing (i.e. NPIs), and 2) endogenous growth rate of disease. To make effective use of the nonlinear and temporal aspects of the data, both factors are implemented as LSTM models, each with a single LSTM layer followed by a dense layer with a single output. To satisfy their output bounds, the dense layers of above factors are followed by sigmoid and softplus activation, respectively.

Importantly, the factorization of function into above stated factors makes it possible to explicitly incorporate the constraint that increasing the stringency of NPIs cannot decrease their effectiveness. This idea is incorporated by constraining first factor to be monotonic with respect to each NPI. Briefly, an LSTM model build on past data is employed as a predictor in a multi-objective setting by way of incorporating specific knowledge about context and actions by processing both of contexts and actions separately and then combining them in a way that incorporates this knowledge into a predictor. In particular, this allows applying known constraints about the effects of context and actions. For example, their effects may be bounded in different ways, and other constraints applied, such as monotonicity.

Following from above, the factored monotonic LSTM (NPI-LSTM) predictor design is validated. Accordingly, the predictor design is compared to a suite of baseline machine learning regression models. These baselines included linear regression, random forest regression (RF), support vector regression (SVR) with an RBF kernel, and feed-forward neural network regression (MLP). Performance of predictor design is illustrated in Attachment A, where the NPI-LSTM methods outperforms the baselines on all metrics, establishing how well data-driven approach works even with limited data.

As understood, an important aspect of any decision system is to estimate confidence in its outcomes. In prescribing NPIs, this means estimating uncertainty in the Predictor, i.e. deriving confidence intervals on the predicted number of future cases. For purposes of present disclosure, uncertainty in model is estimated by an approach called RIO, a Gaussian Process is fit to the original residual errors in the training set. The I/O kernel of RIO utilizes both input and output of the original model so that information can be used where it is most reliable. RIO can be directly applied to any machine-learning model without modifications or retraining, hence chosen for estimating uncertainty in present predictor model for improved accuracy.

In accordance with one other exemplary embodiment of present disclosure, evolutionary prescriptive model is disclosed. The Prescriptor is the heart of ESP approach, and is constructed using modern search techniques such as neural networks. Any of the existing neuroevolution methods could be used to construct the Prescriptor as long as it evolves the entire network including all of its weight parameters: Neural architecture search cannot be used easily since there are no targets (i.e. known optimal NPIs) with which to train it with gradient descent. The most straightforward approach of evolving a vector of weights for a fixed topology is, therefore, used and found to be sufficient in this case.

The Prescriptor model is a neural network with one input layer. This input is the same as the context input of the Predictor. The input layer is followed by a fully-connected hidden layer with an activation function and outputs with the sigmoid activation function. The outputs represent possible NPIs, which will then be input to the Predictor. Each output may be further scaled to represent the corresponding NPI stringency levels. Prescriptor candidates are evaluated according to two objectives: (1) the expected number of cases over predetermined number of days according to the prescribed NPIs, and (2) the total stringency of the prescribed NPIs, serving as a proxy for the cost of the NPIs. Both objectives have to be minimized. After evaluations, candidates are discovered that are increasingly more fit along the two objectives. In the end, the collection of candidates that represent best possible tradeoffs between objectives (the Pareto front, i.e. the set of candidates that are better than all other candidates in at least one objective) are the final result of the experiment. Given a desired balance, the ESP system will find the best to achieve outcome (i.e. with the lowest cost and the lowest number of cases).

However, the data is still noisy for several reasons including: differences in how cases are reported in each country; lack of uniformity in manner of reporting the cases, e.g., United States; varying testing policies and availability from country to country limited detection of cases; some countries, like China, US, and Italy, implemented NPIs at a state/regional level, and it is difficult to express them at the country level; datasets are imperfect, there are mistakes, missing days, double-counted days, etc.

It is also important to note that there is up to a two-week delay between the time a person is infected and the time the case is detected. A similar delay can therefore be expected between the time an NPI is put in places and its effect on the number of cases.

Despite these challenges, it is possible to use the data to train a useful model to predict future cases. In the exemplary embodiment, the models were trained using the "Confirmed-Cases" data for the cases and "Closure and Containment" data for the NPIs. The number of cases was selected as the target for the predictions (instead of number of deaths, which is generally believed to be more reliable), because case numbers are higher and the data is smoother overall. The model also utilizes a full 21-day case history which it can use to uncover structural regularities in the case data. For instance, it discovers that many fewer cases are reported on the weekends in France and Spain.

Given this data, a learned predictor can be designed. For a given country, let $x_n$ be the number of new cases on day n. The goal is to predict $x_n$ in the future. First, consider the minimal epidemic model $$x_n = R_n x_{n-1} => R_n = \frac{x_n}{x_{n-1}}, \quad (4)$$

for some $$R_n \geq 0$$

where the factor $R_n$ is to be predicted. Focusing on such factors is fundamental to epidemiological models, and, when learning a predictive model from data, makes it possible to normalize prediction targets across countries and across time, thereby simplifying the learning task.

Training targets $R_n$ can be constructed directly from daily case data for each country. However, in many countries case reporting is noisy and unreliable, leading to unreasonably high noise in daily $R_n$. This effect can be mitigated by instead forming smoothed targets based on a moving average $z_n$ of new cases:

$$z_n = R_n z_{n-1} => R_n = \frac{z_n}{z_{n-1}}, \quad (5)$$

where $$z_n = \frac{1}{K} \sum_{i=0}^{K-1} x_{n-i}.$$

For this exemplary embodiment, K=7 for all models, i.e. prediction targets are smoothed over the preceding week.

To capture the effects of finite population size and immunity, an additional factor is included that scales predictions by the proportion of the population that could possibly become new cases:

$$z_n = \frac{P - y_{n-1}}{P} R_n z_{n-1} => R_n = \frac{P z_n}{(P - y_{n-1}) z_{n-1}}, \quad (6)$$

where P is the population size, and $y_n = \sum_{i=0}^{n} x_i$ is the total number of recorded cases by day n. Notice that, when evaluating a trained model, the predicted $\hat{x}_n$ can be recovered from a predicted $\hat{R}_n$ by $$\hat{x}_n = \left(\hat{R}_n \frac{P - y_{n-1}}{P} - 1\right) K z_{n-1} + x_{n-K}. \quad (7)$$

Note that this formulation assumes that recovered cases are fully immune: When $P = y_{n-1}$, the number of new cases goes to 0. This assumption can be relaxed in the future by adding a factor to Equation (6) (either taken from the literature or learned) to represent people who were infected and are no longer immune.

The trainable function implementing $\hat{R}_n$ can now be described. The prediction $\hat{R}_n$ should be a function of (1) NPIs enacted over previous days, and (2) the underlying state of the pandemic distinct from the enacted NPIs. For the models in this exemplary embodiment, (1) is represented by the NPI restrictiveness values for the past T=21 days over all N=8 available NPIs, and (2) is represented autoregressively by the T previous values of $R_n$ (or, during forecasting, by the predicted $\hat{R}_n$ when the true $R_n$ is unavailable). Formally, $$\hat{R}_n = f(A_n, r_n),$$

$$\text{with } A_n \in \mathbb{N}_0^{T \times N} \text{ and } r_n \in \mathbb{R}_{\geq 0}^T. \quad (8)$$

In contrast to epidemiological models that make predictions based on today's state only, this data-driven model predicts based on data from the preceding three weeks.

To help the model generalize with a relatively small amount of training data, the model is made more tractable by decomposing f with respect to its inputs:

$$\hat{R}_n = f(A_n, r_n) = (1 - g(A_n)) h(r_n),$$

$$\text{with } g(A_n) \in [0,1] \text{ and } h(r_n) \geq 0. \quad (9)$$

Here, the factor $g(A_n)$ can be viewed as the effect of social distancing (i.e. NPIs), and $h(r_n)$ as the endogenous growth rate of the disease.

To make effective use of the nonlinear and temporal aspects of the data, both g and h are implemented as LSTM models, each with a single LSTM layer of 32 units, followed by a dense layer with a single output. To satisfy their output bounds, the dense layers of g and h are followed by sigmoid and softplus activation, respectively Importantly, the factorization of f into g and h makes it possible to explicitly incorporate the constraint that increasing the stringency of NPIs cannot decrease their effectiveness. This idea is incorporated by constraining g to be monotonic with respect to each NPI, i.e.

$$\min(A - A') \geq 0 => g(A) \geq g(A'). \quad (10)$$

This constraint is enforced by requiring all trainable parameters of g to be non-negative, except for the single bias parameter in its dense layer. This non-negativity is implemented by setting all trainable parameters to their absolute value after each update.

Note that although the model is trained only to predict one day in the future, it can make predictions arbitrarily far into the future given a schedule of NPIs by autoregressively feeding the predicted $\hat{R}_{n+t}$ back into the model as input.

Figure 4:
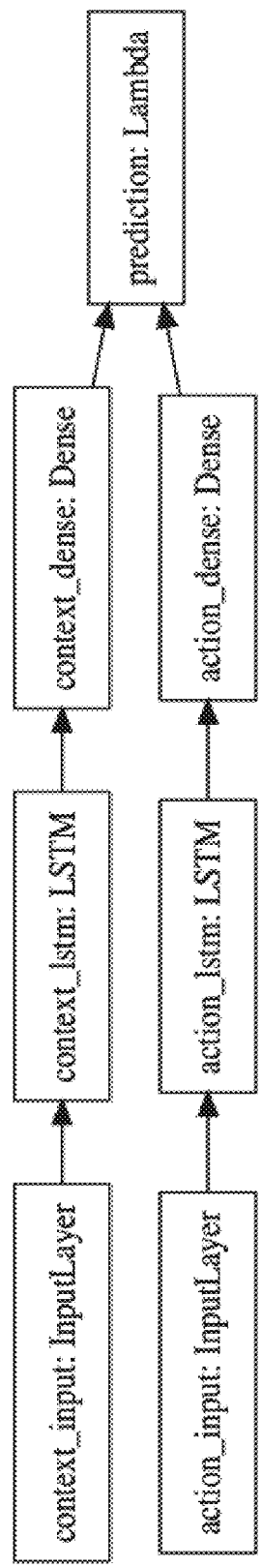
FIG. 4 is a Keras diagram of a model in accordance with a preferred embodiment.

For the experiments discussed herein, the model for f was implemented in Keras. The Keras diagram of the model is shown in FIG. 4. The model is trained end-to-end to minimize mean absolute error (MAE) with respect to targets $R_n$ using the Adam optimizer with default parameters and batch size 32. MAE was used instead of mean squared error (MSE) because it is more robust to remaining structural noise in the training data. The last 14 days of data were withheld from the dataset for testing. For the remaining data, the $R_n$ were clipped to the range [0,2] to handle extreme outliers, and randomly split into 90% for training and 10% for validation during training. The model was trained until validation MAE did not improve for 20 epochs, at which point the weights yielding the best validation MAE were restored. Since the model and dataset are small compared to common deep learning datasets, the model is inexpensive to train. On a 2018 MacBook Pro Laptop with six Intel i7 cores, the model takes 276±31 seconds to train (mean and std. err. computed over 10 independent training runs).

To validate the factored monotonic LSTM (NPI-LSTM) predictor design described above, it was compared to a suite of baseline machine learning regression models. These baselines included linear regression, random forest regression (RF), support vector regression (SVR) with an RBF kernel, and feed-forward neural network regression (MLP). Each baseline was implemented with sci-kit learn, using their default parameters. Each method was trained independently 10 times on the training dataset discussed above. The results on the test dataset (last $T^*=14$ days of the $C=20$ countries with the most cases) were evaluated with respect to four complementary performance metrics. In particular, for the comparisons in this section, training data consisted of data up until May 6, 2020, and test data consisted of data from May 7 to May 20, 2020.

Suppose training data ends on day n. Let $\hat{R}_{n+t}^c$ and $\hat{x}_{n+t}^c$ be the model output and the corresponding predicted new cases (recovered via Equation 7) for the cth country at day n+t. The metrics were:

1) 1-Step $\hat{R}_n$ MAE: This metric is simply the loss the models were explicitly trained to minimize, i.e. minimize $|R_n - \hat{R}_n|$ given the ground truth for the previous 21 days:

$$1/CT^* \Sigma_{c=1}^{C} \Sigma_{t=1}^{T^*} |R_{n+t}^c - \hat{R}_{n+t}^c|. \tag{11}$$

The remaining three metrics are based not on single-step prediction, but the complete 14 day forecast for each country:

2) Raw Case MAE: This is the most intuitive metric, included as an interpretable reference point. It is simply the MAE w.r.t. new cases over the 14 test days summed over all 20 test countries:

$$\Sigma_{c=1}^{C} |\Sigma_{t=1}^{T^*} x_{n+t}^c - \Sigma_{t=1}^{T^*} \hat{x}_{n+t}^c|. \tag{12}$$

3) Normalized Case MAE: This metric normalizes the case MAE of each country by the number of true cases in the 14 day window, so that errors are in a similar range across countries. Such normalization is important for aggregating results over countries that have different population sizes, or are in different stages of the pandemic:

$$\frac{1}{C} \sum_{c=1}^{C} \frac{\left| \sum_{t=1}^{T^*} x_{n+t}^c - \sum_{t=1}^{T^*} \hat{x}_{n+t}^c \right|}{\sum_{t=1}^{T^*} x_{n+t}^c}. \tag{13}$$

(4) Mean Rank: This metric ranks the methods in terms of case error for each country, and then averages over countries. It indicates how often a method will be preferred over others on a country-by-country basis:

$$\frac{1}{C} \sum_{c=1}^{C} \text{rank}\left( \left| \sum_{t=1}^{T^*} x_{n+t}^c - \sum_{t=1}^{T^*} \hat{x}_{n+t}^c \right| \right), \tag{14}$$

where rank(•) returns the rank of the error across all five methods, i.e. the method with the Lowest error receives rank of 0, the next-best method receives rank of 1, and so on.

Of these four metrics, Normalized Case MAE gives the most complete picture of how well a method is doing, since it combines detailed case information of Raw Case MAE with fairness across countries similar to Mean Rank. The results are shown in Table 1. NPI-LSTM outperforms the baselines on all metrics. Interestingly, although RF and SVR do quite well in terms of the loss on which they were trained (1-step $\hat{R}_n$ MAE), the simple linear model outperforms them substantially on the metrics that require forecasting beyond a single day, showing the difficulty that off-the-shelf non-linear methods have in handling such forecasting.

TABLE 1

| Method | Norm. Case | Raw Case | Mean Rank | 1-step $\hat{R}_n$ |
| --- | --- | --- | --- | --- |
| MLP | 2.47 ± 1.22 | 1089126 ± 540789 | 3.19 ± 0.09 | 0.769 ± 0.033 |
| RF | 0.95 ± 0.05 | 221308 ± 8717 | 1.98 ± 0.10 | 0.512 ± 0.000 |
| SVR | 0.71 ± 0.00 | 280731 ± 0 | 1.76 ± 0.09 | 0.520 ± 0.000 |
| Linear | 0.64 ± 0.00 | 176070 ± 0 | 1.63 ± 0.09 | 0.902 ± 0.000 |
| NPI-LSTM | 0.42 ± 0.04 | 154194 ± 14593 | 1.46 ± 0.08 | 0.510 ± 0.001 |

To verify that the predictions are meaningful and accurate, four example scenarios, i.e. four different countries at different stages of the pandemic, are plotted in FIG. 4 (active cases at each day is approximated as the sum of new cases over the prior 14 days). Day 0 represents the point in time when 10 total cases were diagnosed; in each case, stringent NPIs were enacted soon after. The predictor was trained on data up until Apr. 17, 2020, and the predictions started on April 18, with 21 days of data before the start day given to the predictor as initial input. Assuming the NPIs in effect on the start day will remain unchanged, it will then predict the number of cases 180 days into the future. Importantly, during the first 14 days its predictions can be compared to the actual number of cases. For comparison, another prediction plot is generated from the same start date assuming no NPIs from that date on. The figures show that (1) the predictions match the actual progress well, (2) assuming the current stringent NPIs continue, the cases will eventually go to 0, and (3) with no NPIs, there is a large increase of cases, followed by an eventual decrease as the population becomes immune. The predictions thus follow meaningful trajectories.

Figure 5A:
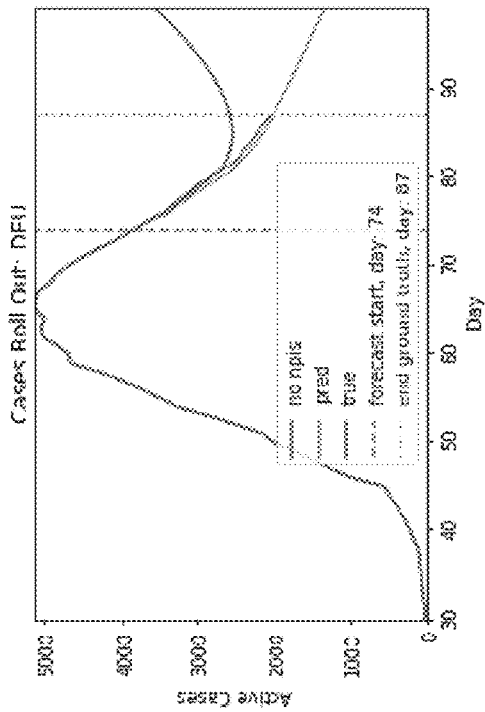
FIGS. 5a, 5b, 5c, 5d illustrate the predictive ability of the NPI-LSTM model Predictor in accordance with a preferred embodiment, wherein actual and projected cases are shown for four sample countries: Italy (FIG. 5a), Germany (FIG. 5b), United States (FIG. 5c) and Belgium (FIG. 5d)
Figure 5B:
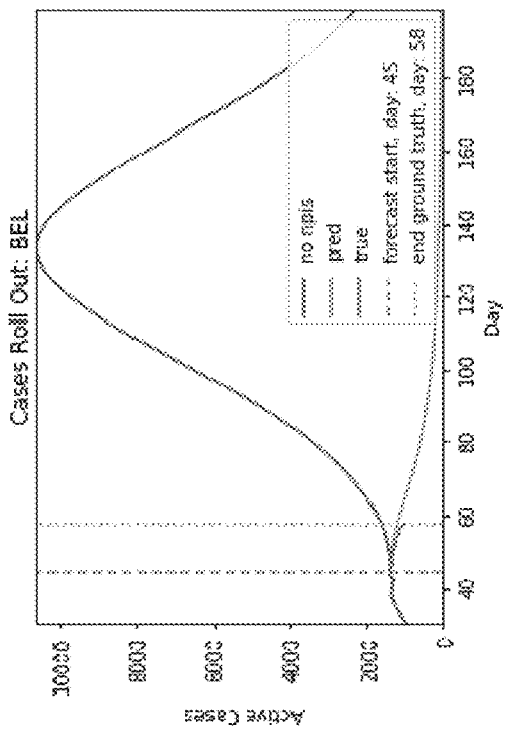
Figure 5C:
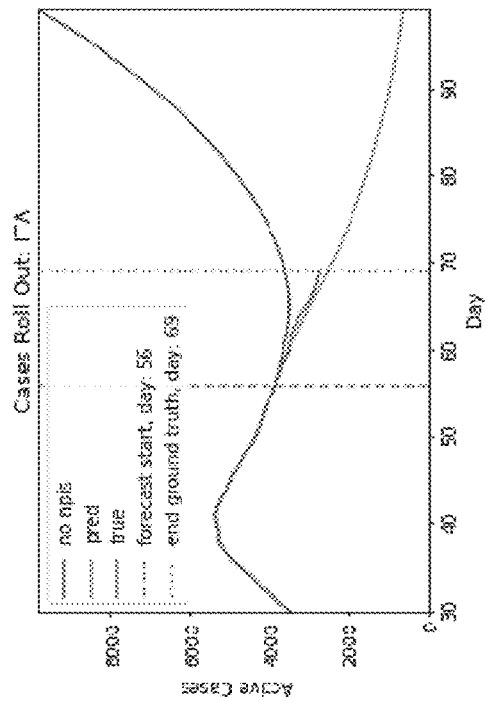
Figure 5D:
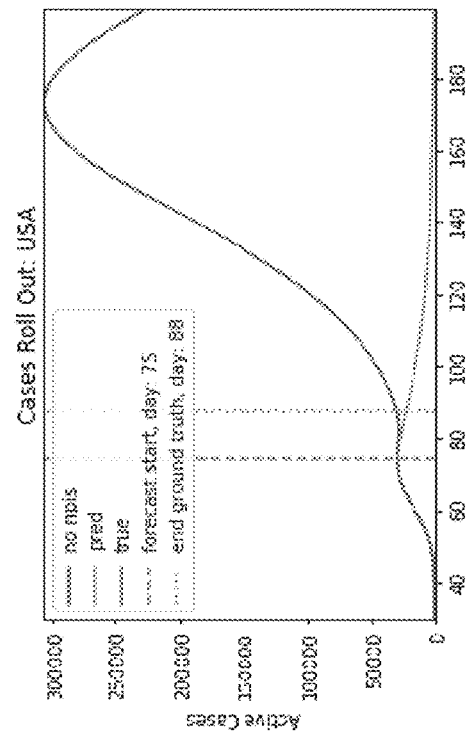

FIGS. 5a-5d illustrate the predictive ability of the NPI-LSTM model Predictor wherein actual and projected cases are shown for four sample countries: Italy (FIG. 5a), Germany (FIG. 5b), United States (FIG. 5c) and Belgium (FIG. 5d). As shown, the model predicts the number of cases accurately for the first 14 days where it can be compared with the actual future data (between the vertical lines). The prolonged 180-day predictions are also meaningful, reducing the number of cases to zero with stringent NPIs, and predicting a major increase followed by an eventual decrease with less stringent NPIs. Thus, with proper constraints, data-driven machine learning models can be surprisingly accurate in predicting the progress of the pandemic even with limited data.

An important aspect of any decision system is to estimate confidence in its outcomes. In prescribing NPIs, this means estimating uncertainty in the Predictor, i.e. deriving confidence intervals on the predicted number of future cases. In simulation models such as those referenced in the Background of the Invention, variation is usually created by running the models multiple times with slightly different initial conditions or parameter values, and measuring the resulting variance in the predictions. With neural network predictors, it is possible to measure uncertainty more directly by combining a Bayesian model with the predictor. Such extended models tend to be less accurate than pure predictive models, and also harder to set up and train.

A recent alternative is to train a separate model to estimate uncertainty in point-prediction models. In this approach, called RIO, a Gaussian Process is fit to the original residual errors in the training set. The I/O kernel of RIO utilizes both input and output of the original model so that information can be used where it is most reliable. In several benchmarks, RIO has been shown to construct reliable confidence intervals. Surprisingly, it can then be used to improve the point predictions of the original model, by correcting them towards the estimated mean. RIO can be applied to any machine learning model without modifications or retraining. It therefore forms a good basis for estimating uncertainty also in the COVID-19 Predictor. A detailed description of RIO can be found in co-owned U.S. patent application Ser. No. 16/879,934 entitled Quantifying the Predictive Uncertainty of Neural Networks Via Residual Estimation With I/O Kernel, which is incorporated herein by reference in its entirety.

In order to extend RIO to time-series predictions, the hidden states of the two LSTM models (before the lambda layer in FIG. 3) are concatenated and fed into the input kernel of RIO. The original predictions of the predictor are used by the output kernel. RIO is then trained to fit the residuals of the original predictions. During deployment, the trained RIO model then provides a Gaussian distribution for the calibrated predictions.

To validate this process empirically with COVID-19 data, the data was preprocessed in four steps: (1) Among the 30 most affected countries in terms of cases, those with the most accurate predictions were selected, resulting in 17 countries with MAE less than 0.04; (2) The outlier days that had an R larger than 2.0 were removed from the data; (3) The earliest 10 days (after the first 21 days) were removed as well, focusing training on more recent data and (4) For each country, 14 days were selected randomly as the testing data, and all the remaining days were used as the training data. The hyperparameters in these steps were found to be appropriate empirically. Table 2 shows the results, wherein % CI=percentage of testing outcomes within estimated confidence intervals.

TABLE 2

| Dataset | Orig. MAE | RIO MAE | 95% CI | 90% CI | 68% CI |
|---|---|---|---|---|---|
| Training | 0.0319 | 0.0312 | 0.952 | 0.921 | 0.756 |
| Testing | 0.0338 | 0.0337 | 0.929 | 0.899 | 0.710 |

The conclusion is that RIO constructs reasonable confidence intervals (CI) at several confidence levels, and slightly improves the prediction accuracy. It can therefore be expected to work well in estimating confidence in the NPI prescription outcomes as well.

However, RIO will first need to be extended to model uncertainty in time series. Because NPI-LSTM forecasts are highly nonlinear and autoregressive, analytic methods are intractable. Instead, given that the predictor model with RIO returns both the mean and the quartiles for $\hat{R}_n$, the quartiles after t days in the future can be estimated via Monte Carlo rollouts. Specifically, for each step in each rollout, instead of predicting $\hat{R}$ and feeding it back into the model to predict the next step, $\hat{R}$ is sampled from the Gaussian distribution returned by RIO, and this sample is fed back into the model. Thus, after T* steps, a sample is generated from the forecast distribution. Given several such samples (100 in the experiments discussed herein), the upper and lower quartile are computed empirically for all forecasted days $1 \leq t \leq T^*$.

Thus, RIO makes it possible to estimate uncertainty in the predictions, which in turn helps the decision maker interpret and trust the results, i.e. how reliable the outcomes are for the recommendations that the Prescriptors generate.

Whereas many different models could be used as a Predictor, the Prescriptor is the heart of the ESP approach, and needs to be constructed using modern search techniques. The process of evolving neural networks for this task in accordance with a preferred embodiment is described herein. A number of example strategies are presented from the Pareto front, representing trade-offs between objectives, as well as examples for countries at different stages of the pandemic, and counterfactual examples comparing possible vs. actual outcomes. General conclusions are drawn on which NPIs matter the most, and how they could be implemented most effectively.

Figure 6:
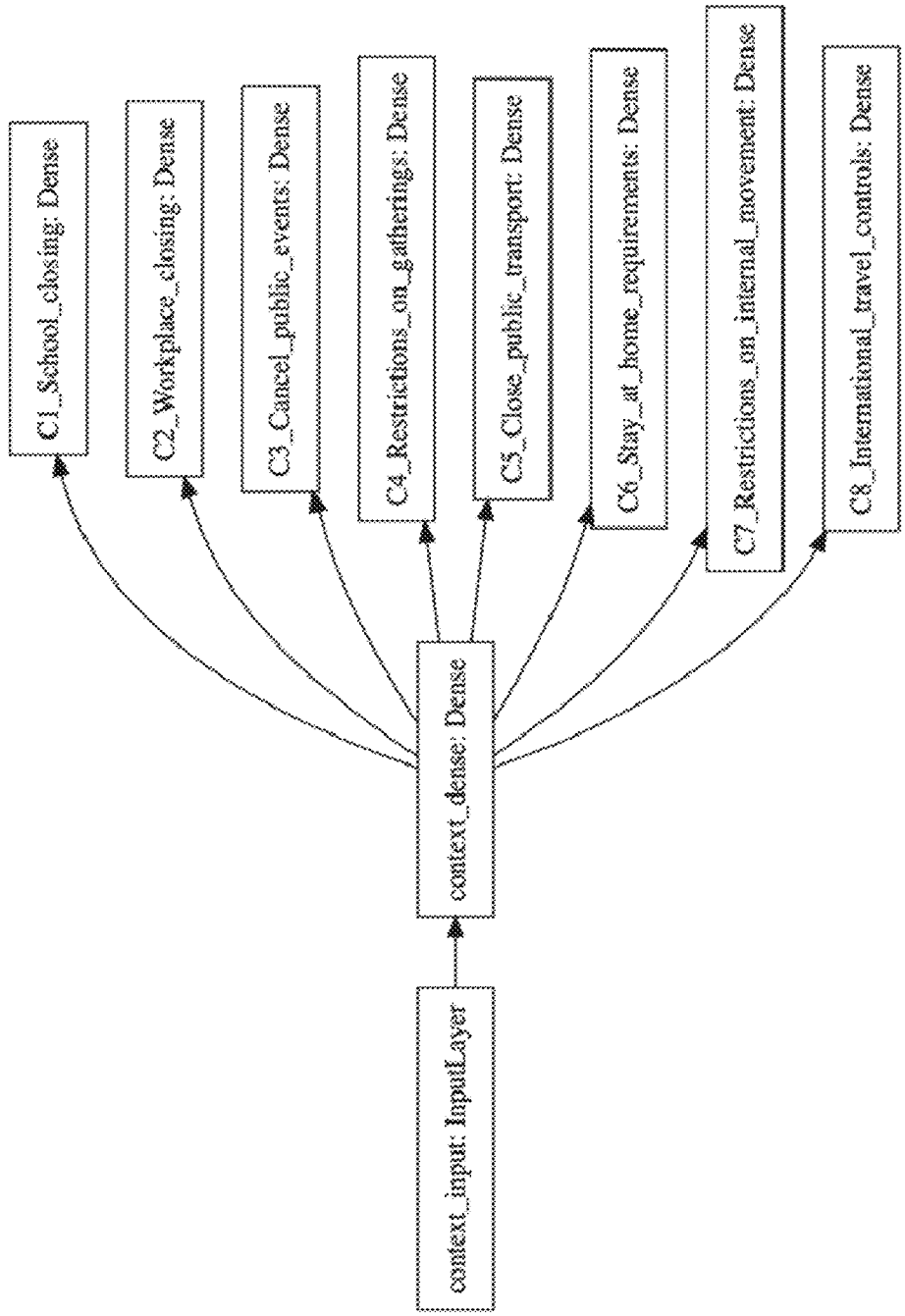
FIG. 6 is a Prescriptor neural network in accordance with a preferred embodiment.

Any of the existing neuroevolution methods known to those skilled in the art could be used to construct the Prescriptor as long as it evolves the entire network including all of its weight parameters. The most straightforward approach of evolving a vector of weights for a fixed topology was found to be sufficient in the current application. The Prescriptor model (FIG. 6) is a neural network with one input layer of size 21, corresponding to case information $R_{n-t}$ (as defined in Equation (6)) for the prior 21 days. This input is the same as the context input of the Predictor. The input layer is followed by a fully-connected hidden layer of size 32 with the tan h activation function, and eight outputs (of size one) with the sigmoid activation function. The outputs represent the eight possible NPIs which will then be input to the Predictor. Each output is further scaled and rounded to represent the NPI stringency levels: within [0,2] for 'Cancel public events', 'Close public transport', and 'Restrictions on internal movement'; [0,3] for 'School closing', 'Workplace closing', and 'Stay at home'; [0,4] for 'Restrictions on gatherings' and 'International travel controls'.

The initial population uses orthogonal initialization of weights in each layer with a mean of 0 and a standard deviation of 1. The population size is 250 and the top 6% of the population is carried over as elites. Parents are selected by tournament selection of the top 20% of candidates using the NSGA-II algorithm. Recombination is performed by uniform crossover at the weight-level, and there is a 20% probability of multiplying each weight by a mutation factor, where mutation factors are drawn from $\mathcal{N}(1,0.1)$.

Prescriptor candidates are evaluated according to two objectives: (1) the expected number of cases according to the prescribed NPIs, and (2) the total stringency of the prescribed NPIs (i.e. the sum of the stringency levels of the eight NPIs), serving as a proxy for their economic cost. Both measures are averaged over the next 180 days and over the 20 countries with the most deaths in the historical data, which at the time of the experiment were United States, United Kingdom, Italy, France, Spain, Brazil, Belgium, Germany, Iran, Canada, Netherlands, Mexico, China, Turkey, Sweden, India, Ecuador, Russia, Peru, Switzerland. Both objectives have to be minimized.

Starting from the most recent day in the dataset for each country, each Prescriptor is fed with the last 21 days of case information. Its outputs are used as the NPIs at the evaluation start date, and combined with the NPIs for the previous 20 days. These 21 days of case information and NPIs are given to the Predictor as input, and it outputs the predicted case information for the next day. This output is used as the most recent input for the next day, and the process continues for the next 180 days. At the end of the process, the average number of predicted new cases over the 180-day period is used as the value of the first objective. Similarly, the average of daily stringencies of the prescribed NPIs over the 180-day period is used as the value for the second objective.

Figure 7:
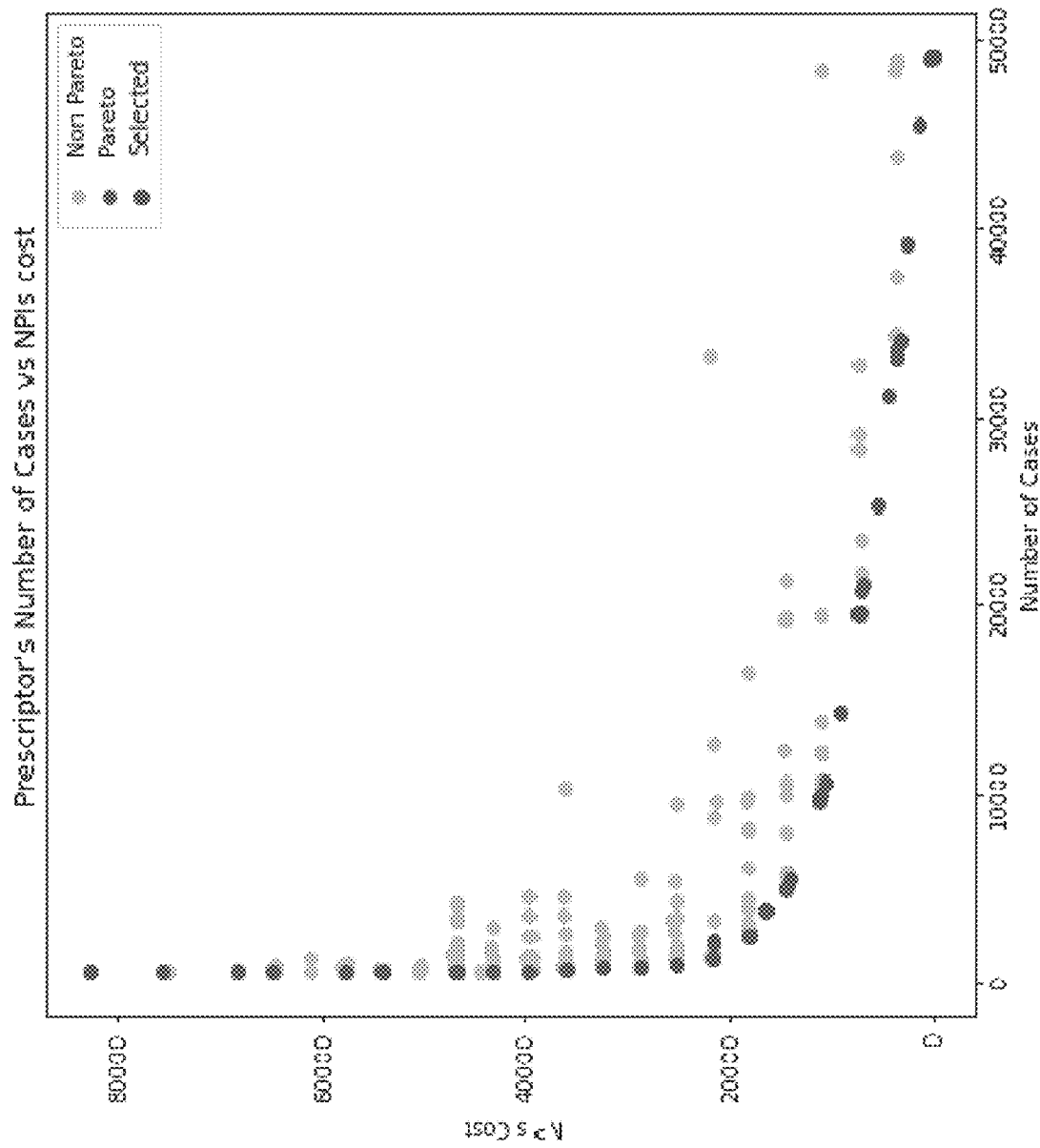
FIG. 7 charts fitness of the final population of candidates along the case number and cost objectives in accordance with a preferred embodiment.

After each candidate is evaluated in this manner, the next generation of candidates is generated. Evolution is run for 100 generations, or approximately 18 hours on an 8-CPU host. During the course of evolution, candidates are discovered that are increasingly fit along the two objectives. In the end, the collection of candidates that represent best possible tradeoffs between objectives (the Pareto front, i.e. the set of candidates that are better than all other candidates in at least one objective) is the final result of the experiment. FIG. 7 illustrates fitness of the final population along the case and cost objectives. The candidates at the lower left side are on the Pareto front, representing the best tradeoffs. Those in red are used in the examples below and in the interactive demo (numbered 0 to 19 from left to right). They are the 20 candidates with the highest crowding distance in NSGA-II. The other candidates in the Pareto front are in dark blue and other final population candidates in light blue. From this collection, it is up to the human decision maker to pick the tradeoff that achieves a desirable balance between cases and cost. Or put in another way, given a desired balance, the ESP system will find the best solution to achieve it (i.e. with the lowest cost and the lowest number of cases).

Figure 8A:
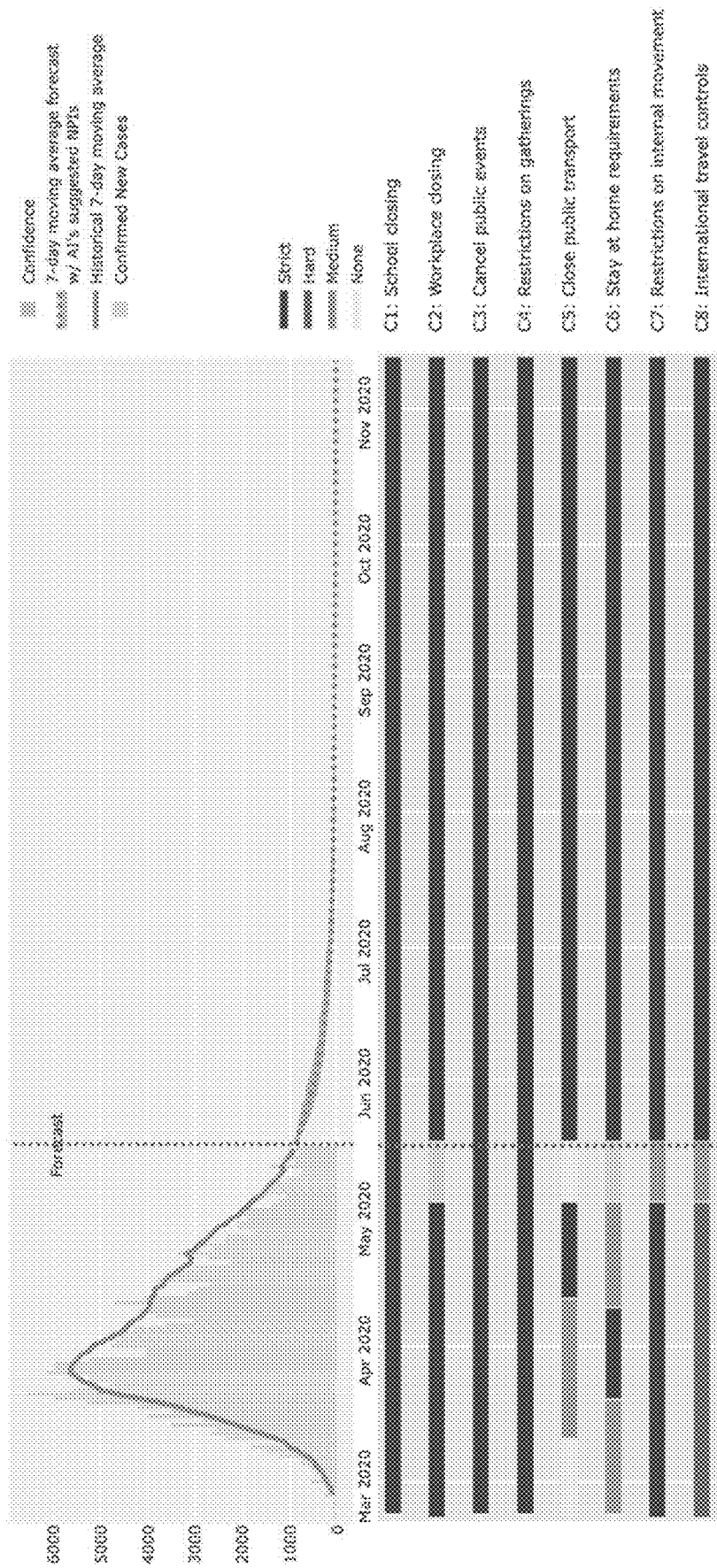
FIGS. 8a, 8b, 8c, 8d represents the uncertainty of the prediction, i.e., areas between 25th and 75th percentiles of the 100 Monte Carlo rollouts under uncertainty estimated through RIO in accordance with a preferred embodiment.
Figure 8B:
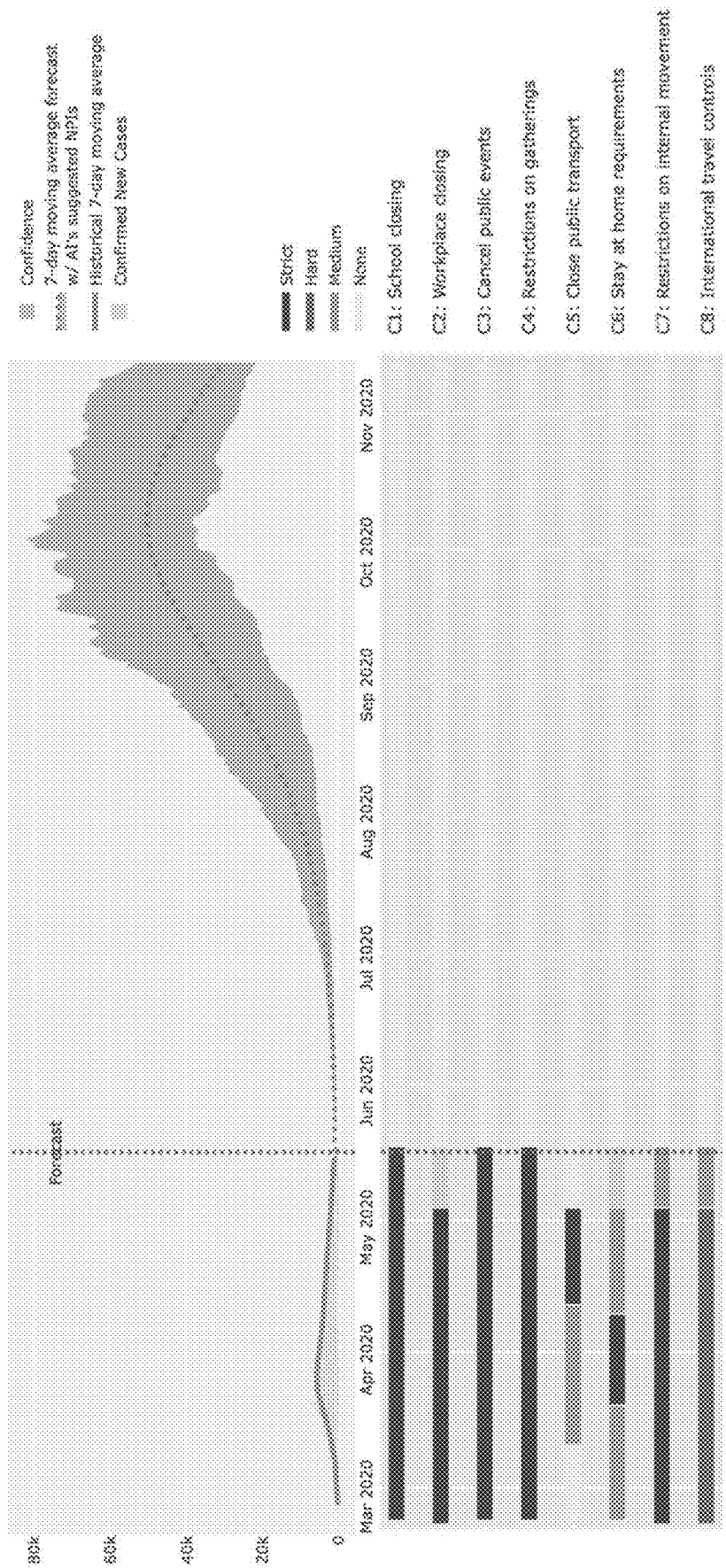
Figure 8C:
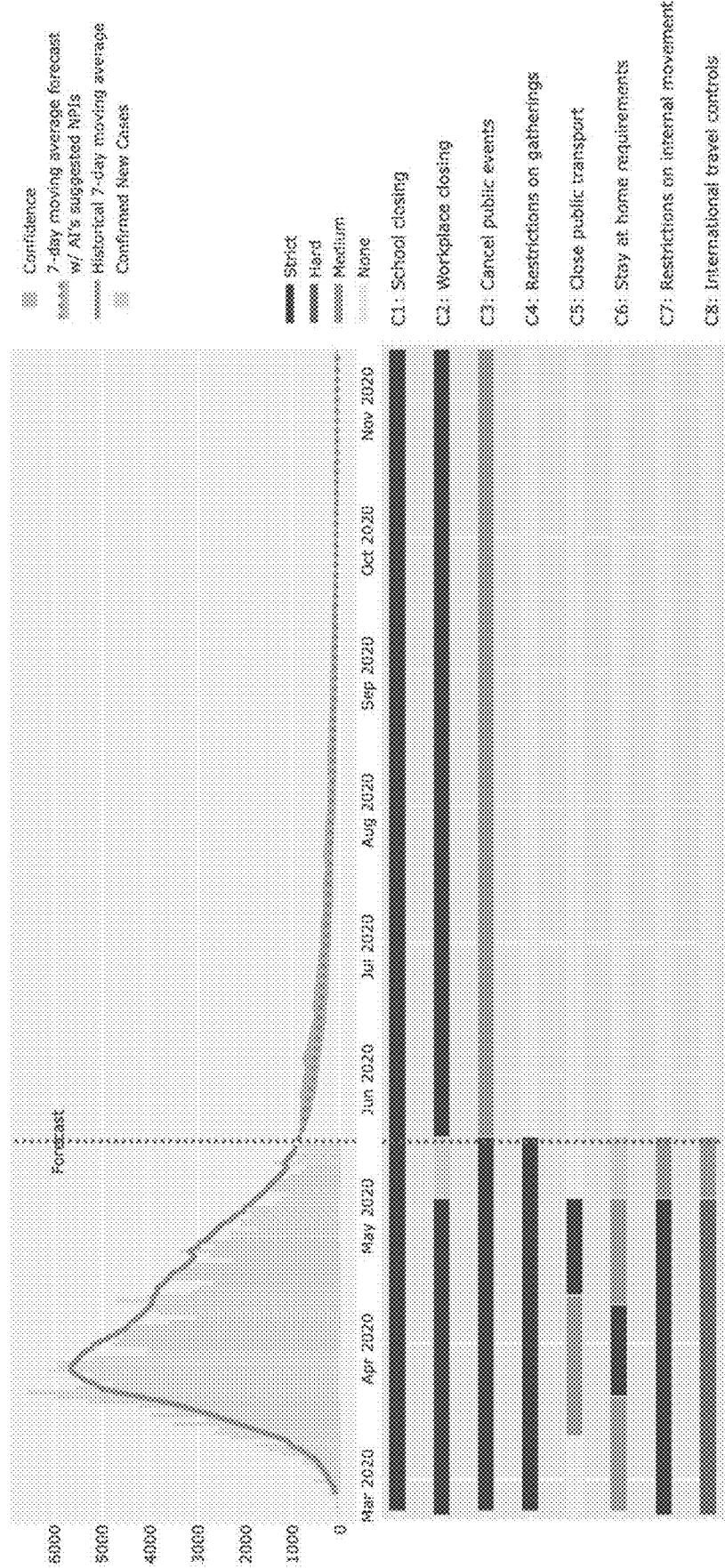
Figure 8D:
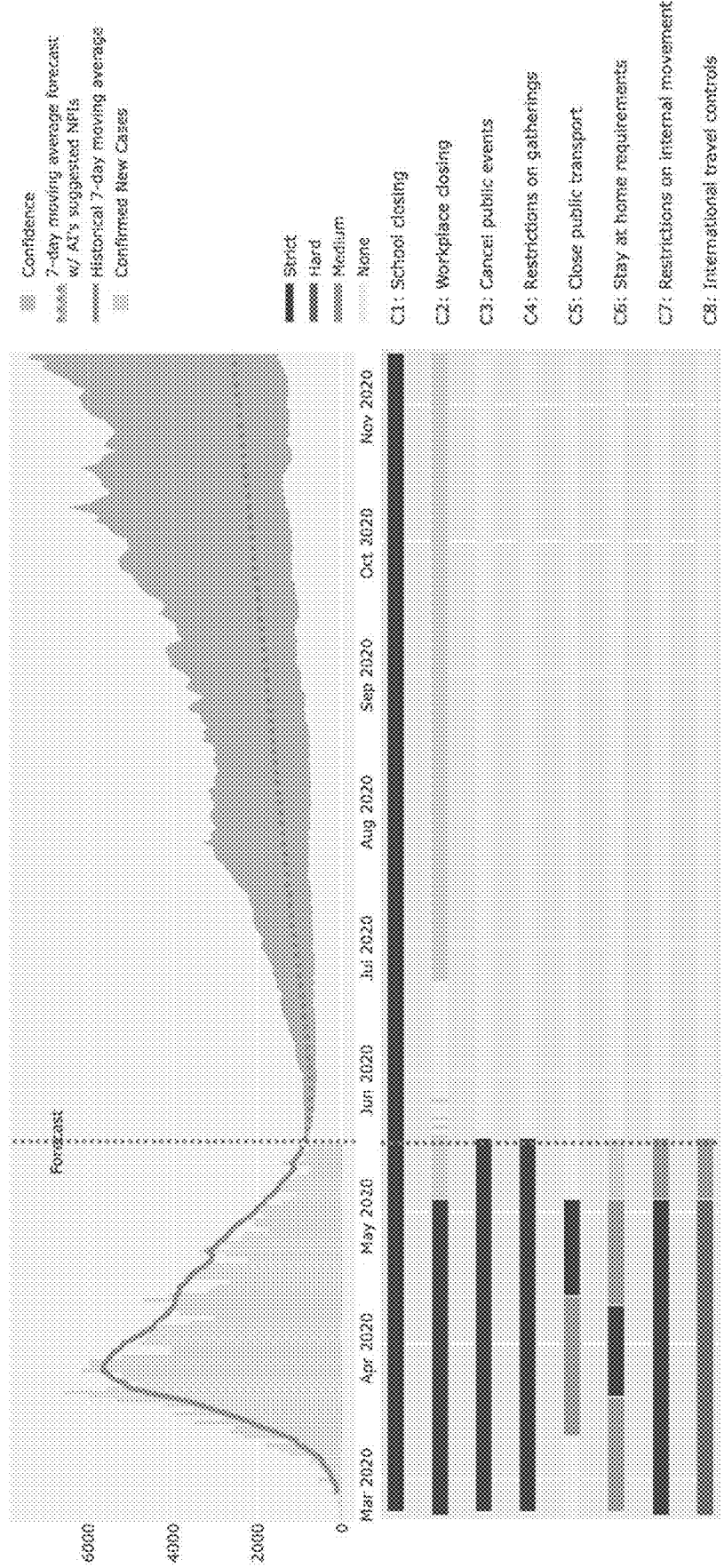

To illustrate these different tradeoffs, FIGS. 8a-8d show the NPI Prescriptions and the resulting forecasts for four different Prescriptors from the Pareto front for one country, Italy, on May 18, 2020. Daily cases are shown as orange vertical bars and their seven-day moving average as the orange line. The vertical line indicates the start of the forecast, and the gray area represents uncertainty around the prediction. The NPI prescriptions are shown below the case plot as horizontal bars, with color representing stringency. FIG. 8a is a Prescriptor that minimizes the number of cases recommends a full set of NPIs at their maximum level of stringency. FIG. 8b is a Prescriptor that minimizes the NPI stringency recommends lifting all NPIs, which is likely to result in a high number of cases. FIG. 8c is a Prescriptor that tries to minimize the number of cases while lifting as many NPIs as possible recommends keeping restrictions mostly on schools and workplaces. FIG. 8d is a Prescriptor that tries to reduce the cost more by opening up workplaces completely may result in cases climbing up. In this manner, the human decision maker can explore the tradeoffs between cases and cost, and the ESP system will recommend the best ways to achieve it.

The Prescriptor that minimizes cases prescribes the most stringent NPIs across the board, and as a result, the number of cases is minimized effectively. The Prescriptor that minimizes NPI stringency lifts all NPIs right away, and the number of cases is predicted to explode as a result. The Prescriptor in FIG. 8c was chosen from the middle of the Pareto front (from FIG. 7), and it represents one particular way to balance the two objectives. It lifts most of the NPIs, allows some public events, and keeps the schools and workplaces closed. As a result, the number of cases is still minimized, albeit slightly slower than in the most stringent case. Lifting more of the NPIs, in particular workplace restrictions, is likely to cause the number of cases to start climbing. In this manner, the decision maker may explore the Pareto front, finding a point that achieves the most desirable balance of cases and cost for the current stage of the pandemic.

The shadowed area in FIGS. 8a-8d represents the uncertainty of the prediction, i.e., areas between 25th and 75th percentiles of the 100 Monte Carlo rollouts under uncertainty estimated through RIO. The width of the shadowed area is normalized to match the scale of the forecasts (dotted line). It is often asymmetric because there is more variance in how the pandemic can spread than how it can be contained. Whereas uncertainty is narrow with stringent Prescriptors (FIGS. 8a, 8c) it often increases significantly with time with less stringent ones. The increase can be especially dramatic with Prescriptors with minimal NPIs, such as those in FIGS. 8b, 8d. Part of the reason is that at the time these forecasts were made, not much training data existed yet about this stage of the pandemic (i.e. the stage where countries are lifting most NPIs after the peak of the pandemic has passed). However, the result also suggests that such minimal-NPI prescriptions are fragile, making the country vulnerable to subsequent waves of the pandemic (see also FIGS. 8c, 8d).

Figure 9A:
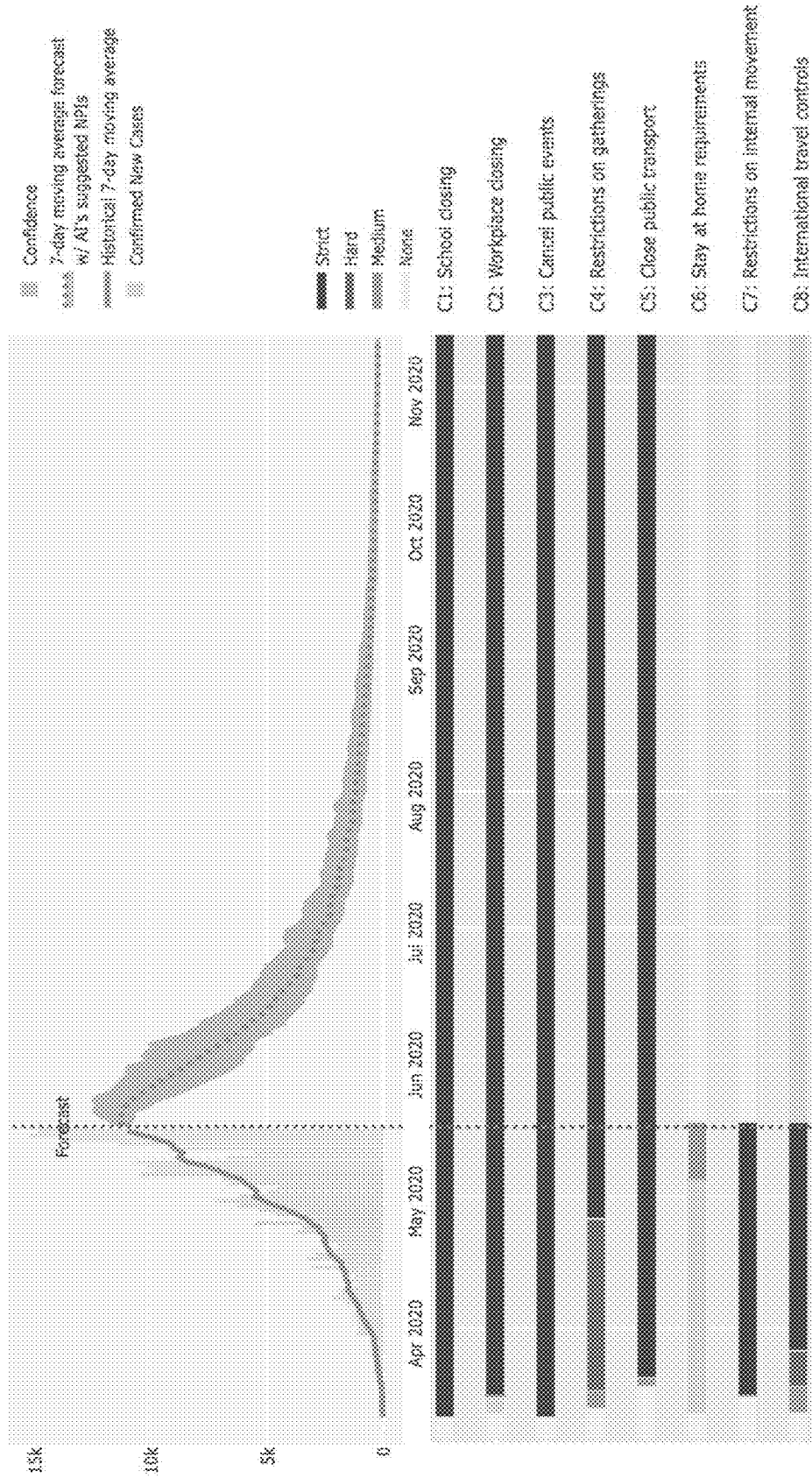
FIGS. 9a, 9b, 9c, 9d illustrate comparison of tradeoff prescriptions for countries at different stages of the COVID-19 pandemic in accordance with a preferred embodiment.
Figure 9B:
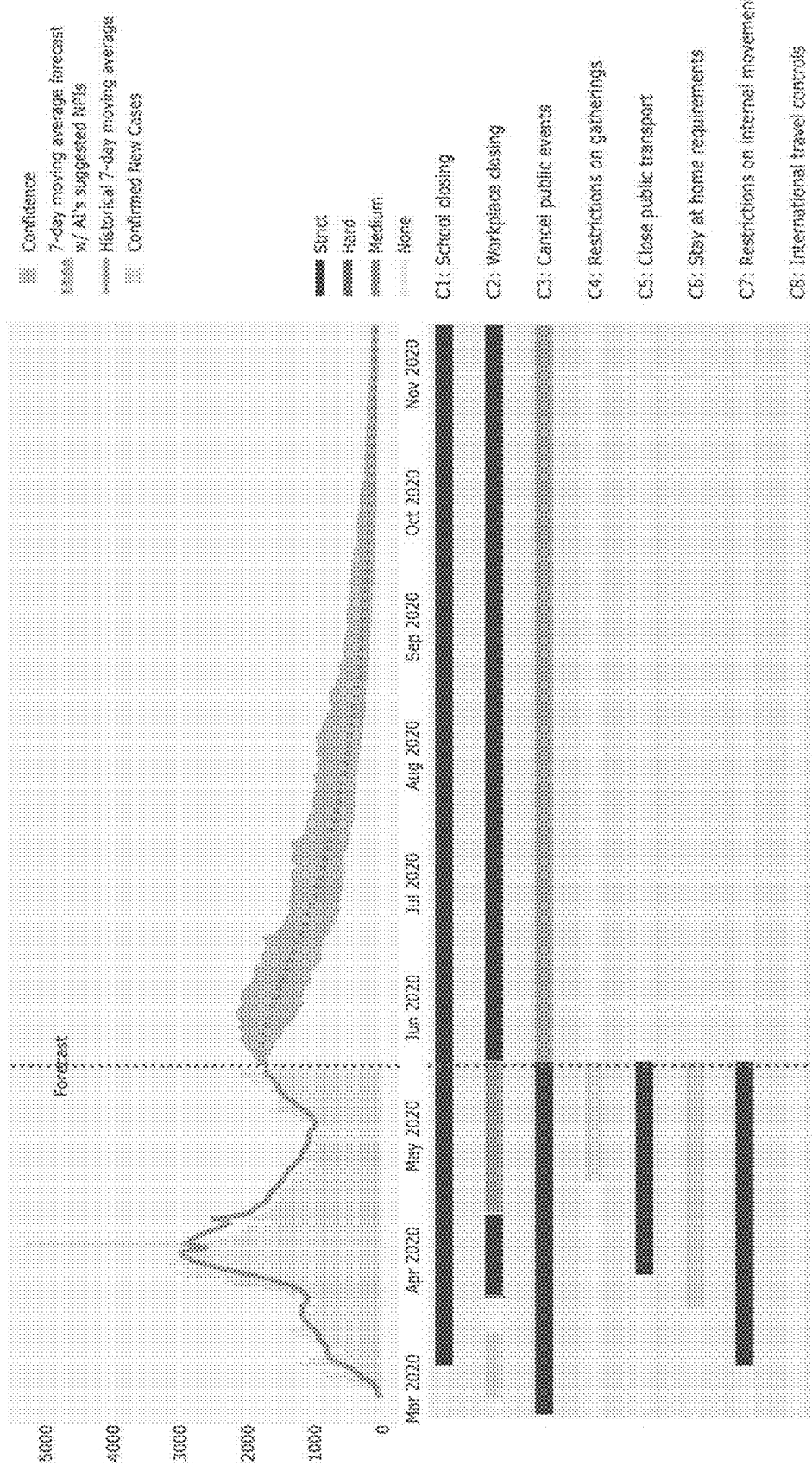
Figure 9C:
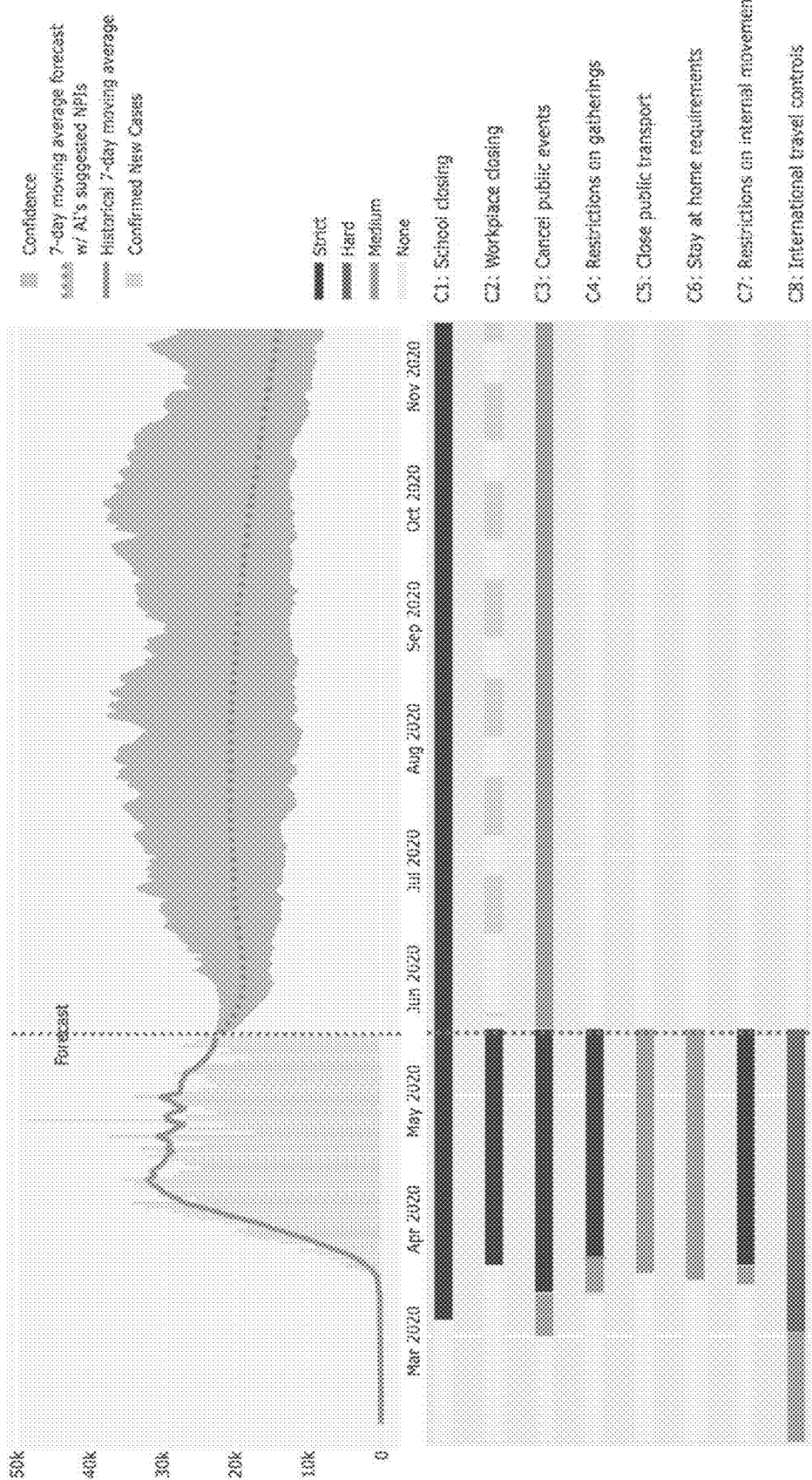
Figure 9D:
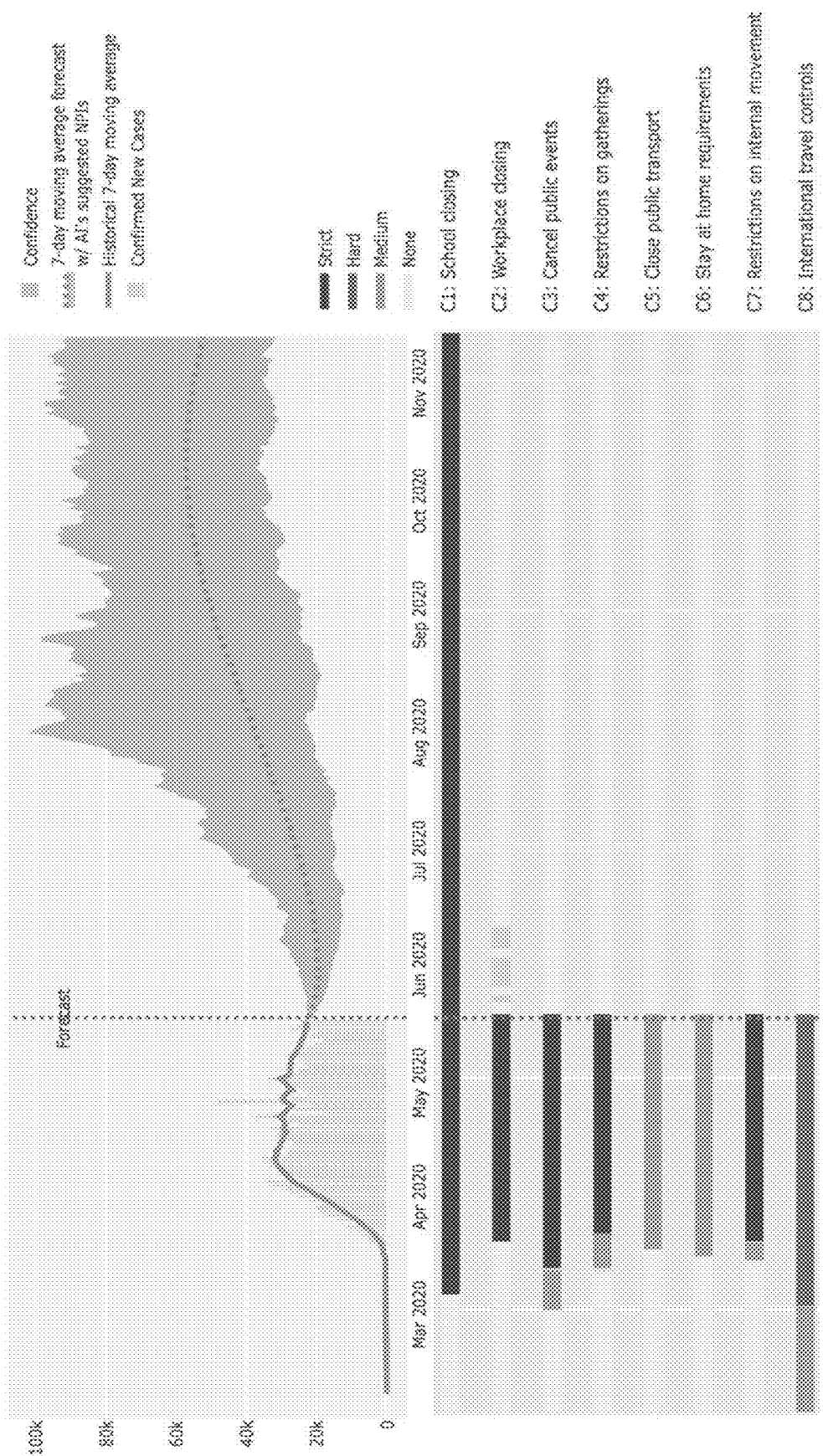

To illustrate this process, FIG. 9a-9d shows possible choices for three different countries at different stages of the pandemic on May 18, 2020. For Brazil, where the pandemic is still spreading rapidly at this point, a relatively stringent Prescriptor 4 allows some freedom of movement without increasing the cases much compared to full lockdown (FIG. 9a). For Iran, where there is a danger of a second wave, Prescriptor 6 provides more stringent NPIs to prevent cases from increasing, still limiting the restrictions to schools, workplaces and public events (FIG. 9b). For US, where the number of cases has been relatively flat, a less stringent Prescriptor 7 may be chosen, limiting restrictions to schools, workplaces, and public events (FIG. 9c). In contrast, if NPIs are lifted too much, e.g. by opening up the workplaces and allowing public events, high numbers of cases are predicted to return (FIG. 9d). Interestingly, in all these cases as well as in FIG. 9c, schools and workplaces are subject to restrictions while others are lifted. Also, Prescriptor 7 (FIG. 9c) often includes an alternation of stringency levels, suggesting a way to reduce the cost of the NPI while potentially keeping it effective. Thus, evolution discovers where NPIs may have the largest impact, and can suggest creative ways of implementing them.

Interestingly, across several countries at different stages of the pandemic, a consistent pattern emerges: in order to keep the number of cases flat, other NPIs can be lifted gradually, but workplace and school restrictions need to be in effect much longer. Indeed these are the two activities where people spend a lot of time with other people indoors, where it is possible to be exposed to significant amounts of the virus. In other activities, such as gatherings and travel, they may come to contact with many people briefly and often outdoors, mitigating the risk. Therefore, the main conclusion that can already be drawn from these prescription experiments is that it is not the casual contacts but the extended contacts that matter. Consequently, when planning for lifting NPIs, attention should be paid to how workplaces and schools can be opened safely.

Another interesting conclusion can be drawn from FIG. 9c: Alternating between weeks of opening workplaces and partially closing them may be an effective way to lessen the impact on the economy while reducing cases. This solution is interesting because it shows how evolution can be creative and find surprising and unusual solutions that are nevertheless effective. While on/off alternation of school and workplace closings may sound unwieldy, it is a real possibility. Note also that it is a creative solution discovered in a highly limited search space. There are no options in the Prescriptor's output for e.g. alternating remote and in-person work, extending school to wider hours, improving ventilation, moving classes outside, requiring masks, or other ways of possibly reducing exposure. How to best implement such distancing at schools and workplaces is left for human decision makers at this point; the model, however, makes a suggestion that coming up with such solutions may make it possible to lift the NPIs gradually, and thereby avoid secondary waves of cases.

Accordingly, in the early stages, the ESP approach suggests how to "flatten the curve", i.e. what NPIs should be implemented in order to slow down the spread of the disease. At later stages, ESP may recommend how the NPIs can be lifted and the economy restarted safely. A third role for the ESP approach is to go back in time and evaluate counterfactuals, i.e. how well NPI strategies other than those actually implemented could have worked. It may thus be possible to draw conclusions not only about the accuracy and limitations of the modeling approach, but also lessons for future waves of the current pandemic, for new regions where it is still spreading, as well as for future pandemics.

Figure 10A:
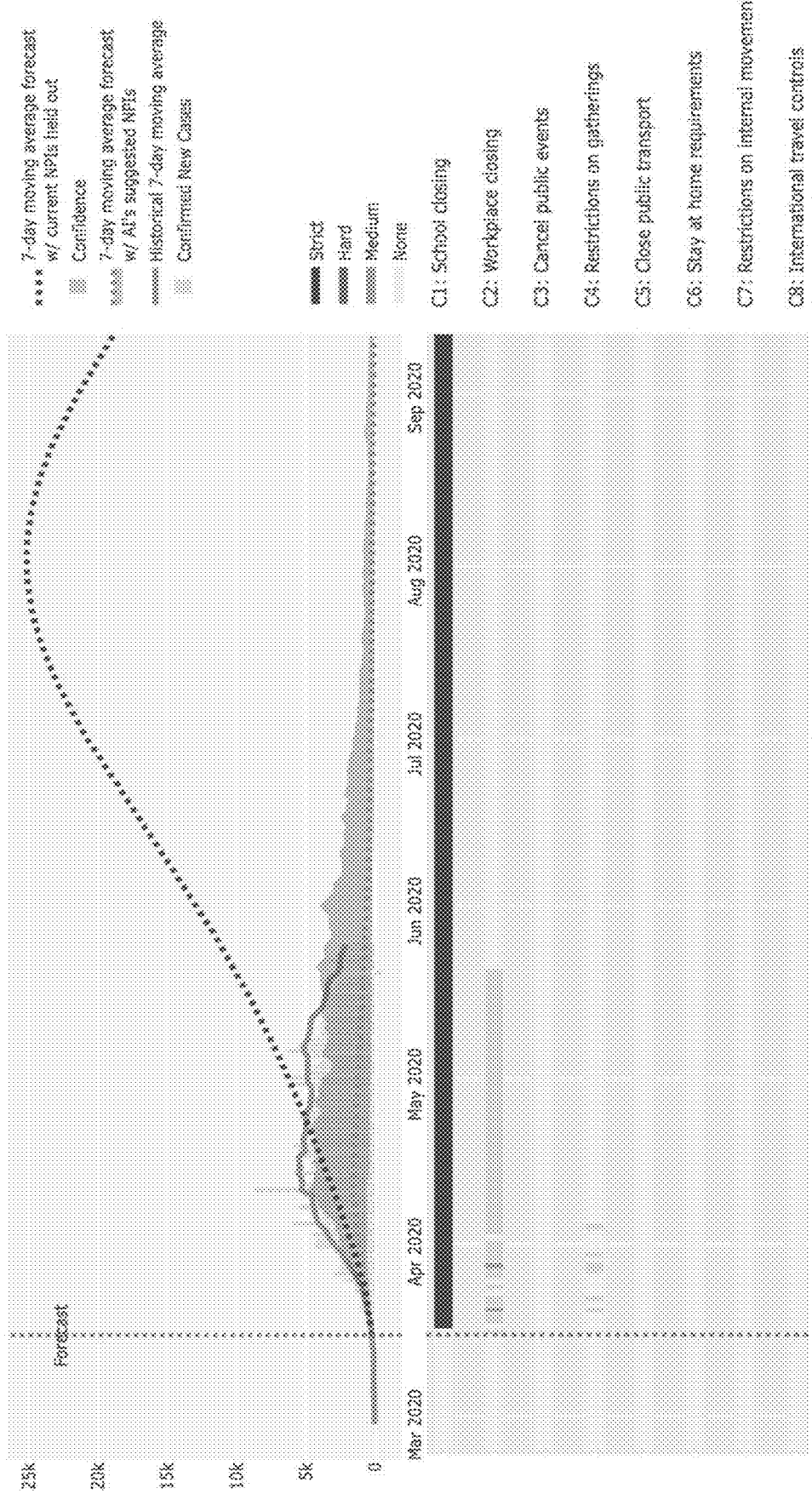
FIGS. 10a, 10b illustrate evaluation of model with counterfactuals in accordance with a preferred embodiment.
Figure 10B:
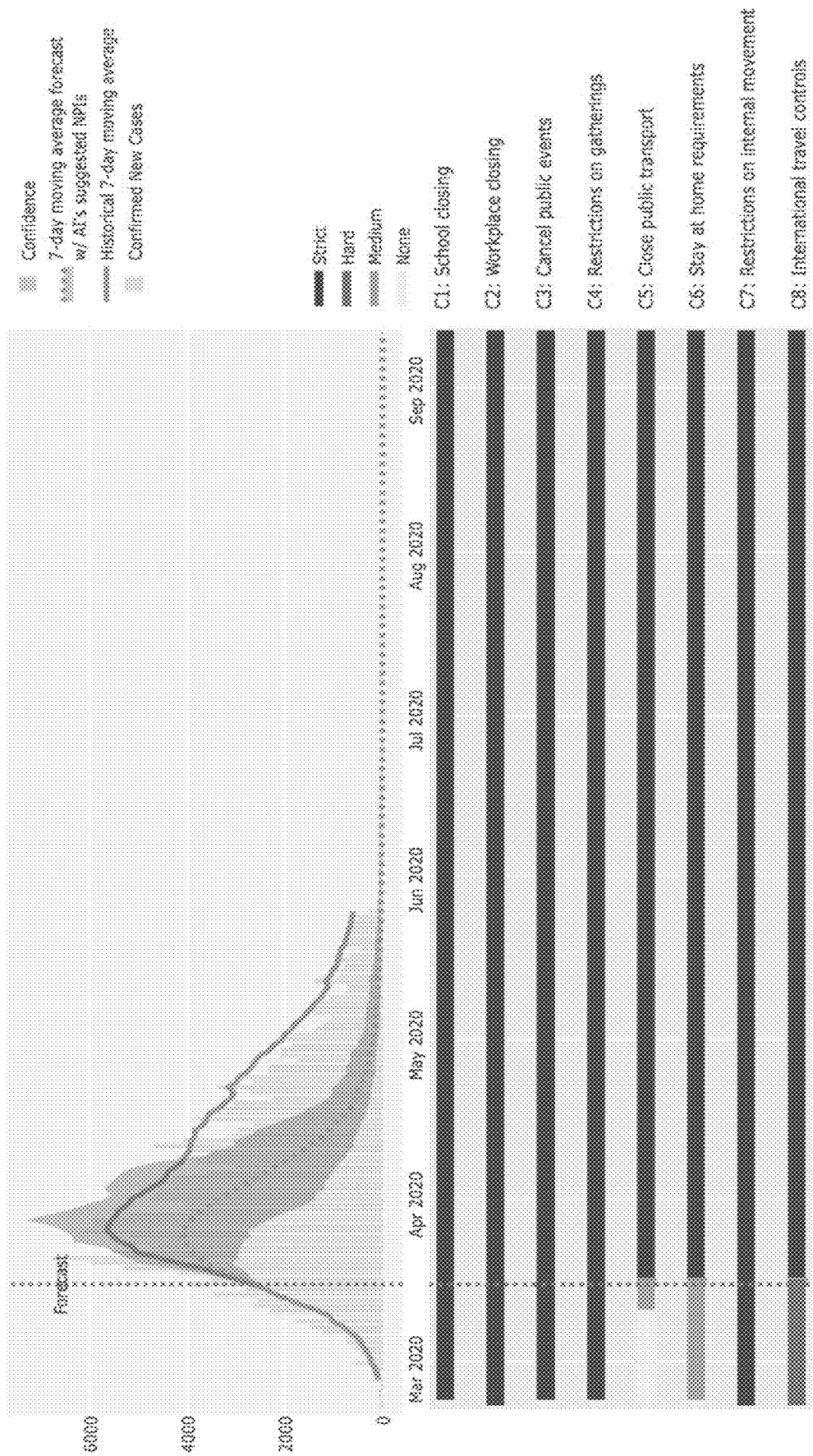

Referring to FIGS. 10a and 10b, going back in time to make prescriptions makes it possible to evaluate how accurate the model is and to draw lessons for the remainder of this pandemic and future pandemics. In FIG. 10a, we see that after an initial phase of mild NPIs, a lockdown implemented in the UK on Mar. 24, 2020, averted a sharp rise in cases. However, Prescriptor 8 (FIG. 10a) would have recommended earlier NPIs, including closing schools on Mar. 16, 2020, that could have resulted in an even better outcome without a full lockdown.

Some of the limitations of the data-driven approach also become evident in retrospective studies. For instance Italy, where the pandemic took hold before most of the rest of the world, was supposed to be in a lockdown on March 16th (which started already on February 23rd). Yet, the model predicts that under such a lockdown (suggested e.g. by Prescriptor 0 for that date), the number of cases should have been considerably smaller than they actually were (FIG. 10b). The uncertainty is wide, but the model's prediction is remarkably different from those of many other countries. Part of the reason may be that the population in Italy did not adhere stringently to the NPIs at that point; after all, the full scale of the pandemic was not yet evident. The population may also have been older and more susceptible than elsewhere. The data used to train the model comes from 20 different countries and at a later stage of the pandemic spread, and these populations may have followed social distancing more carefully—therefore, the model's predictions on the effectiveness of lockdowns may be too optimistic for Italy. Even with the uncertainty, this result suggests that local factors like culture, economy, population demographics, density, and mobility, may need to be taken into account in the models. It also suggests that the implementation of NPIs need to be sensitive to such factors in order to be effective.

Figure 11:
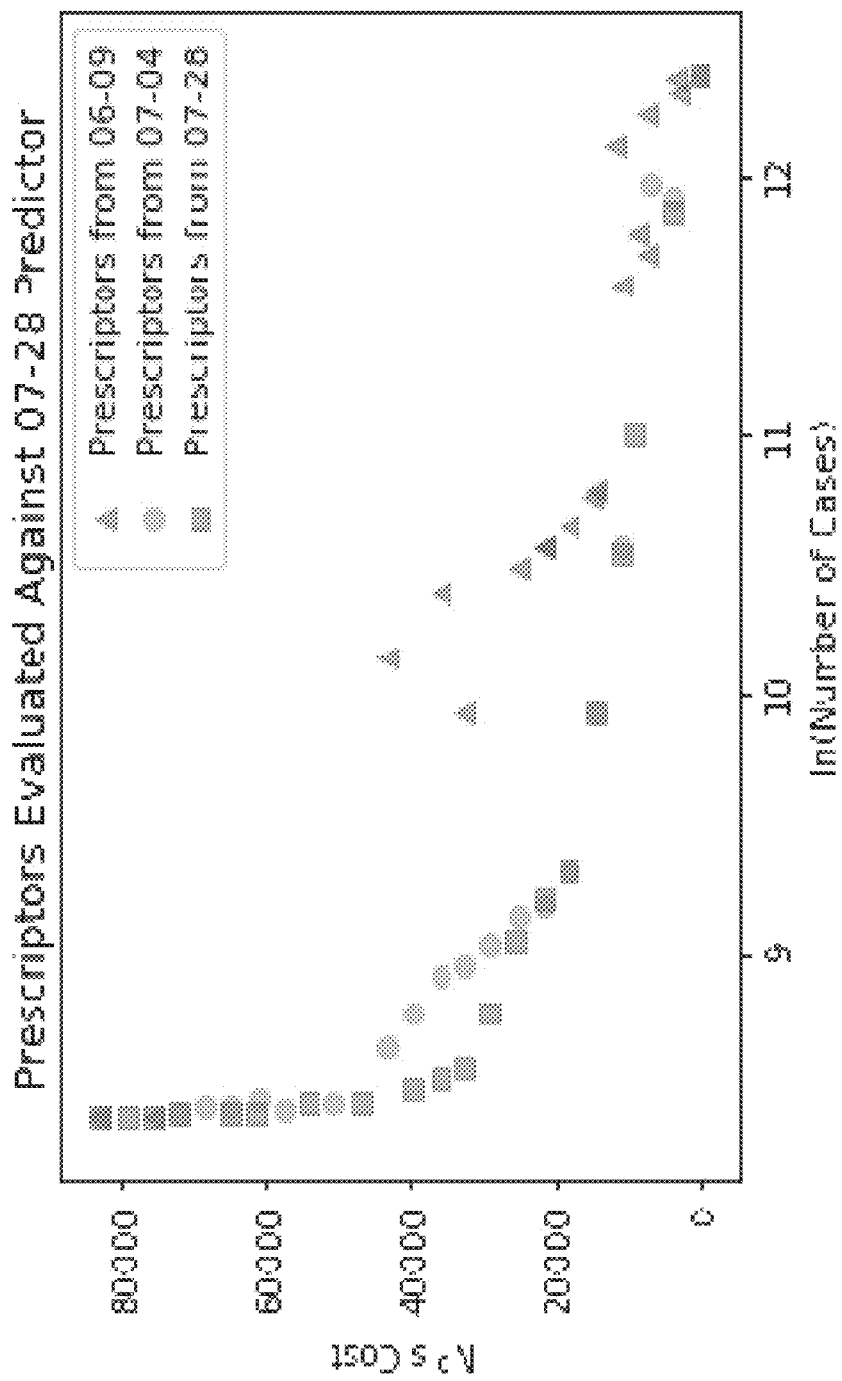
FIG. 11 illustrates the improvement of Prescriptors over time in accordance with a preferred embodiment.

Retrospective studies also show that more data helps make better prescriptions: The Pareto front moves towards the bottom left corner over time, demonstrating that evolution finds Prescriptors that are able to minimize cases and stringency better (FIG. 11). In FIG. 11, the Prescriptors from the Pareto fronts on June 9th, July 4th, and July 28th were run for 180 days from July 28th against the Predictor from July 28th. The later Prescriptors are closer to the bottom left corner, indicating that when evolved with more experienced Predictors, they minimize cases and stringency better. The prescription profiles also change, suggesting that different NPI strategies are needed at different stages of the pandemic. For instance workplace restrictions and stay at home requirements become more important. These profiles partly reflect better decisions, and partly the changing nature of the pandemic. Eventually, once the pandemic has run its course, it should be possible to do a longitudinal study and separate those two factors.

One skilled in the art appreciates that the model may be updated with more data as it becomes available. The models can be extended to predicting and minimizing deaths and hospitalizations as well as number of cases. Such a multitask learning environment should make predictions in each task more accurate. More data may make it possible to use more fine-grained NPIs as well as data on more fine-grained locations, such as US counties. COVID-19 testing and treatment will hopefully improve as well so that the outcome measures will become more reliable. As vaccinations become available, the approach can be extended to include vaccination policies such as prioritizing target populations, conducting campaigns, and implementing concurrent NPIs. In other words, data will improve in volume, relevance, accuracy, and extent, all of which will help make the predictors more precise, and thereby improve prescriptions throughout the pandemic.

It will also be appreciated that outcomes may be improved by taking advantage of multiple prediction models, including more traditional compartmental and network models discussed in the Background. General assumptions about the spread of the disease are built in to these models, and they can thus serve as a stable reference when data is otherwise lacking in a particular case. For instance, while the data was not comprehensive enough to generalize to Italy early in the pandemic (FIG. 9c), it might have been possible to parameterize a traditional model to perform more accurately. On the other hand, it is sometimes hard to estimate the parameters that traditional models require, and data-driven models can be more mode accurate in specific cases. A particularly promising approach might be to form an ensemble from these models and combine their predictions systematically to maximize accuracy.

Another way to make the system more accurate and useful is to improve the outcome measures. Currently the cost of the NPIs is proxied based on how many of them are implemented and at what stringency level. It may be possible to develop more accurate measures based on a variety of economic indicators, such as unemployment, consumer spending, and GNP. They need to be developed for each country separately, given different social and economic structures. With such measures, ESP would be free to find surprising solutions that, while stringent, may not have as high an economic impact.

The retrospective example of Italy in FIG. 10b suggests that it may be difficult to transfer conclusions from one country to another, and to make accurate recommendations early on in the epidemic. Additional analysis could include systematically analyzing how much data and what kind of data is necessary. For instance, if the model had been developed based on the data from China, would it have worked for Iran and Italy? Or after China, Iran, and Italy, would it have worked for the US and the rest of Europe? That is, how much transfer is there between countries and how many scenarios does the model need to see before it becomes reliable? The lessons can be useful for the COVID-19 pandemic already, as well as for future pandemics.

A main consideration with the ESP approach in general is that the historical data needs to be comprehensive enough so that the predictor learns to evaluate even prescriptions that are novel. In other applications of ESP (such as growth recipes for agriculture and designs for web interfaces), a broad range of prescriptions were generated synthetically to make sure they covered the space broadly. Whereas such a process is not possible in the NPI optimization domain, it turned out not to be necessary since the over 180 countries in the dataset represented such a large variety of situations and responses at different stages of the pandemic that learning a robust predictive model was, in fact, possible.

The ability to discover creative solutions, like alternating openings and closures in FIG. 9c, is an important advantage of the evolutionary search approach, but care has to be taken to make sure they are safe. If the predictor cannot evaluate them accurately (because it has never seen them before), unexpected detrimental outcomes may result. In the NPI optimization domain, this problem is unlikely to arise, for three reasons: (1) such prescriptors are unlikely to fare well across several countries and several generations, and are likely to be eliminated from the population; (2) an isolated unreliable prescription would result in high uncertainty and be discarded; (3) creativity in this application is limited to recombinations and time sequences of restrictions: as long as these elements exist in the data, evolution can combine and repeat them to discover a general principle (such as closing schools and workplaces, or repeating an opening and closing pattern). Thus, creativity is limited to a space that makes sense. More generally, ESP applications should include similar limits and sanity checks to avoid unwanted effects. Even in such a limited space there is often room to discover useful principles, as demonstrated in the preferred embodiments described herein.

In applications where safety is paramount, it may be possible to use RIO (discussed above and in detail in co-owned U.S. patent application Ser. No. 16/879,934 entitled Quantifying the Predictive Uncertainty of Neural Networks Via Residual Estimation With I/O Kernel, which is incorporated herein by reference in its entirety) to discount candidates with unsafe prescriptions, perhaps as an additional objective. It could be included late in the evolutionary search process so that evolution can explore and discover novel solutions for most of the run, with reliability and safety emphasized in the end.

The neural network models in the current implementation have relatively simple recurrent and feedforward architectures, compared to current deep learning models of image and language processing. Much of real-world decision-making is based on tabular data, and it is likely that such architectures will be sufficient in most applications. However, metalearning and AutoML techniques, such as hyperparameter optimization and neural architecture search, could be applied to such tabular networks as well. The processing needs may be different in these tasks, and metalearning may discover design choices that improve their performance.

Figure 2C:
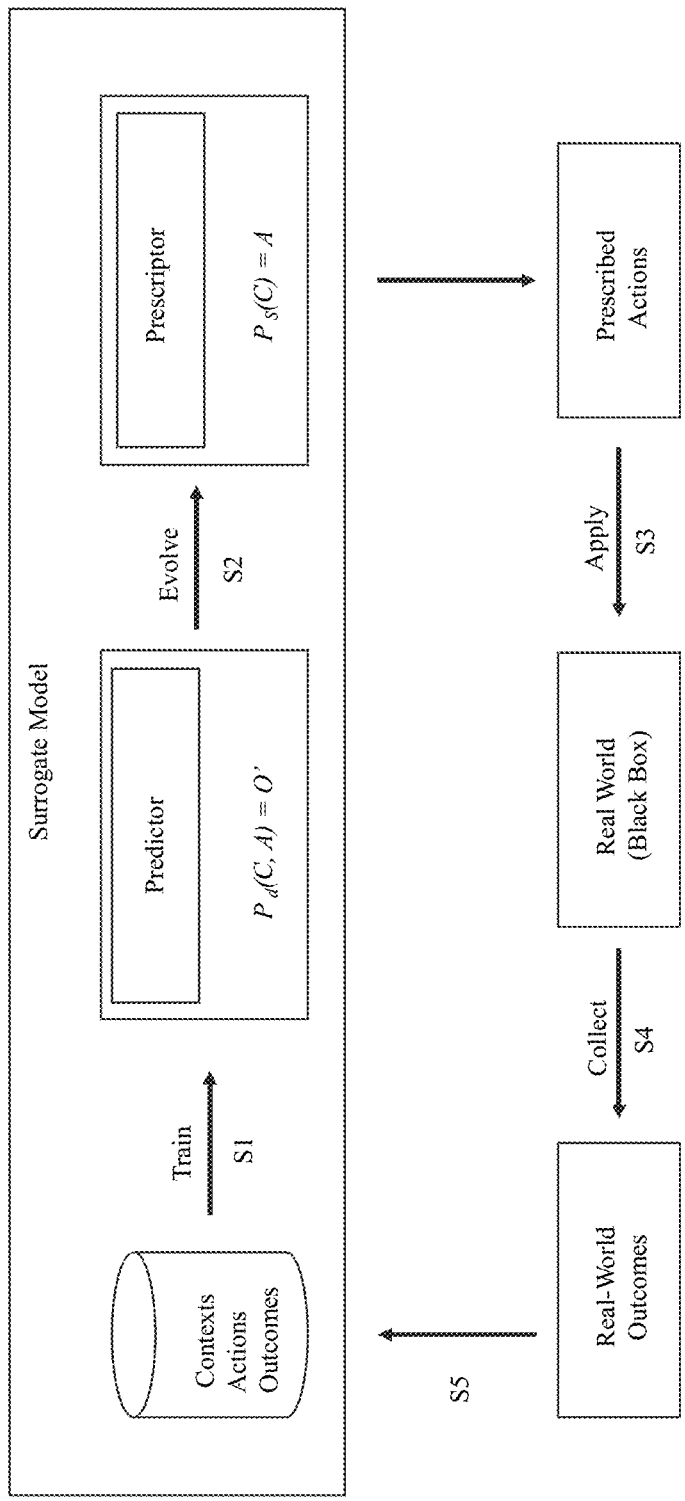

Another interesting extension is to take into account that the Predictor and Prescriptor models in many applications are continually developed in the ESP outer loop, as described in FIG. 2c. Instead of training the models from scratch each time the data is updated, it should be possible to continue training with new data included. Such an approach is straightforward for the Predictor, but with the Prescriptor, it is necessary to ensure that prolonged evolution does not converge the population, making future innovations difficult. If implemented correctly, it may even increase the robustness of solutions. Techniques known to those skilled in the art for diversity maintenance, enhanced evolvability, and multiproblem transfer may prove useful in this role.

Any decision-support system, especially one in domains with many stakeholders with conflicting interests, needs to be trustworthy. More specifically, it needs to estimate confidence in its decisions and predictions, allow users to utilize their expert knowledge and explore alternatives, and explain the decision recommendations. The first step was already taken in this study by applying the RIO uncertainty estimation method to the predictions. This approach may be improved further by grouping the countries according to original predictor performance, then training a dedicated RIO model for each group. In this way, each RIO model focuses on learning the predictive uncertainty of countries with similar patterns, so that the estimated confidence intervals become more reliable. This uncertainty can be used by the Prescriptor to make safer decisions.

Second, a prescription "scratchpad" can be included, allowing the user to not only see the prescription details, but also modify them by hand. In this manner, before any prescriptions are deployed, the user can utilize expert knowledge that may not be available for ESP. For instance, some NPIs in some countries may not be feasible or enforceable at a given time. The interface makes it possible to explore alternatives, and see the resulting outcome predictions immediately. In this manner, the user may find more refined prescriptions than those proposed by ESP, or convince him/herself that they are unlikely to exist. The scratchpad functionality is described in co-owned U.S. patent application Ser. No. 17/209,623 entitled Framework For Interactive Exploration, Evaluation, and Improvement of AI-Generated Solutions, which is incorporated herein by reference in its entirety.

Third, currently the prescriptions are generated by an evolved neural network, which may perform well in the task, but does not provide an explanation of how and why it arrived at a given prescription. In the future, it may be possible to evolve explicit rule sets for this task. Rule sets are readable, specifying which feature values in the context lead to which prescriptions. They can be evolved as prescriptors themselves, or separately to imitate the neural network prescriptors. Thus, like RIO provides a model of uncertainty for the predictions, evolved rule sets can provide a model of explainability for the prescriptions, making it easier for human decision makers to understand and trust the system. Examples of explainable-ESP (E-ESP) may be found in co-owned U.S. patent application Ser. No. 16/902,013 entitled Process and System Including Explainable Prescriptions Through Surrogate-Assisted Evolution, which is incorporated herein by reference in its entirety.

While the embodiments described herein demonstrate the potential value of ESP in coping with the COVID-19 pandemic, the application is not so limited. The general approach can be used to allow decision makers to minimize the impact of future pandemics, as well as improve responses to other natural and man-made disasters, and improve social policies in general. In many such domains, the first step towards adopting such AI-based decision support is likely to be simulations based on historical data.

The foregoing description is a specific embodiment of the present disclosure. It should be appreciated that this embodiment is described for purpose of illustration only, and that those skilled in the art may practice numerous alterations and modifications without departing from the spirit and scope of the invention. It is intended that all such modifications and alterations be included insofar as they come within the scope of the invention as claimed or the equivalents thereof.

The invention claimed is:

1. A system for automatic discovery of non-pharmaceutical intervention (NPI) strategies to optimize one or more objectives related to an epidemiological event, comprising:
a continuously trainable predictor neural network model, $P_d(C, A)=O$, implemented on a processor, the predictor neural network model being configured to receive input data, the input data including context information (C) and actions (A) performed in a given context, and predict an outcome (O) based on the input data, wherein the outcome includes data for the one or more objectives;
a database for storing updated input data, wherein the updated input data is used to continuously train the predictor neural network model over time;
a prescriptor neural network model, $P_s(C)=A$, implemented on a processor, the prescriptor neural network model being configured to
receive context information as input data, wherein the context information includes epidemiological event data; and
output actions that optimize the one or more objectives as outcomes corresponding to the context, wherein the output actions include changes to the implementation of one more non-pharmaceutical interventions (NPIs);
wherein the prescriptor neural network model is evolved over multiple generations using the predictor neural network model as a surrogate.

2. The system of claim 1, wherein the predictor neural network model is a Long Short-Term Memory (LSTM) model.

3. The system of claim 1, wherein the context information (C) and actions (A) data is time series data.

4. The system of claim 3, wherein the predictor neural network model is decomposed into separate factors for context and actions.

5. The system of claim 4, wherein each of the separate factors is a Long Short-Term Memory (LSTM) model.

6. The system of claim 1, wherein the one or more objectives related to an epidemiological event are selected from number of cases, number of hospitalizations and number of deaths.

7. The system of claim 1, wherein the context information including epidemiological event data is selected from the group consisting of: number of confirmed cases, number of hospitalizations, number of deaths, and number of recovered patients, per country, region, and day.

8. The system of claim 1, wherein the one or more non-pharmaceutical interventions (NPIs) actions are selected from the group consisting of: school closing; workplace closing; cancellation of public events; restrictions on gatherings; public transportation closing; stay at home requirements; restrictions on internal movement and restrictions on international travel.

9. The system of claim 8, wherein each of the one or more non-pharmaceutical interventions (NPIs) actions can be implemented at different levels of stringency.

10. A computer-implemented process for automatic discovery of non-pharmaceutical intervention (NPI) strategies to optimize one or more objectives related to an epidemiological event, comprising:
training a predictor neural network model, $P_d(C, A)=O$, implemented on a processor, the predictor neural network model being configured to receive input training data, the input historical training data sets (C, A, O) including context information (C), actions (A) performed in a given context, and outcomes (O) resulting from action performed in the given context;
evolving a prescriptor neural network model, $P_s(C)=A$, implemented on a processor, wherein the prescriptor neural network model is evolved over multiple generations using the trained predictor neural network model as a surrogate, the prescriptor neural network model being configured to
receive context information as input data, wherein the context information includes epidemiological event data; and
output actions that optimize the one or more objectives as outcomes corresponding to the received context information, wherein the output actions include changes to the implementation of one more non-pharmaceutical interventions (NPIs).

11. The computer-implemented process of claim 10, wherein the predictor neural network model is trained with supervised methods.

12. The computer-implemented process of claim 10, wherein the predictor model is a Long Short-Term Memory (LSTM) model.

13. The computer-implemented process of claim 10, wherein the context information (C) and actions (A) data is time series data.

14. The computer-implemented process of claim 13, wherein the predictor neural network model is decomposed into separate factors for context and actions.

15. The computer-implemented process of claim 14, wherein each of the separate factors is a Long Short-Term Memory (LSTM) model.

16. The computer-implemented process of claim 10, wherein the one or more objectives related to an epidemiological event are selected from number of cases, number of hospitalizations and number of deaths.

17. The computer-implemented process of claim 16, wherein the context information including epidemiological event data is selected from the group consisting of: number of confirmed cases, number of hospitalizations, number of deaths, and number of recovered patients, per country, region, and day.

18. The computer-implemented process of claim 17, wherein the one or more non-pharmaceutical interventions (NPIs) actions are selected from the group consisting of: school closing; workplace closing; cancellation of public events; restrictions on gatherings; public transportation closing; stay at home requirements; restrictions on internal movement and restrictions on international travel.

19. The computer-implemented process of claim 18, wherein evolving a prescriptor neural network model, $P_s(C)=A$ includes:
establishing an initial population of candidate prescriptor neural network models, wherein each candidate prescriptor neural network model includes prescribed actions for a given context, the prescribed actions including recommended changes to the implementation of one or more non-pharmaceutical interventions (NPIs);

selecting a subset of candidate prescriptor neural network models from the initial population; and evaluating, using the trained predictor neural network model as a surrogate, each candidate prescriptor neural network model in the subset in accordance with an evaluation of two NPI-related factors impacted by the prescribed actions, the two NPI-related factors including an expected number of cases according to the prescribed NPIs and the total stringency of the prescribed NPIs.

20. At least one non-transitory computer-readable medium storing instructions that, when executed by a computer, perform a process for automatic discovery of non-pharmaceutical intervention (NPI) strategies to optimize one or more objectives related to an epidemiological event, comprising:

training a predictor neural network model, $P_d(C, A)=O$, the predictor model being configured to receive input training data, the input historical training data sets (C, A, O) including context information (C), actions (A) performed in a given context, and outcomes (O) resulting from action performed in the given context;

evolving a prescriptor neural network model, $P_s(C)=A$, wherein the prescriptor neural network model is evolved over multiple generations using the trained predictor neural network model as a surrogate, the prescriptor neural network model being configured to receive context information as input data, wherein the context information includes epidemiological event data, and output actions that optimize the one or more objectives as outcomes corresponding to the received context information, wherein the output actions include changes to the implementation of one or more non-pharmaceutical interventions (NPIs).

21. The at least one non-transitory computer-readable medium of claim 20, wherein the predictor neural network model is trained with supervised methods.

22. The at least one non-transitory computer-readable medium of claim 20, wherein the predictor neural network model is a Long Short-Term Memory (LSTM) model.

23. The at least one non-transitory computer-readable medium of claim 20, wherein the context information (C) and actions (A) data is time series data.

24. The at least one non-transitory computer-readable medium of claim 23, wherein the predictor neural network model is decomposed into separate factors for context and actions.

25. The at least one non-transitory computer-readable medium of claim 24, wherein each of the separate factors is a Long Short-Term Memory (LSTM) model.

26. The at least one non-transitory computer-readable medium of claim 20, wherein the one or more objectives related to an epidemiological event are selected from number of cases, number of hospitalizations and number of deaths.

27. The at least one non-transitory computer-readable medium of claim 26, wherein the context information including epidemiological event data is selected from the group consisting of: number of confirmed cases, number of hospitalizations, number of deaths, and number of recovered patients, per country, region, and day.

28. The at least one non-transitory computer-readable medium of claim 27, wherein the one or more non-pharmaceutical interventions (NPIs) actions are selected from the group consisting of: school closing; workplace closing; cancellation of public events; restrictions on gatherings; public transportation closing; stay at home requirements; restrictions on internal movement and restrictions on international travel.

29. The at least one non-transitory computer-readable medium of claim 28, wherein evolving a prescriptor neural network model, $P_s(C)=A$ includes:

establishing an initial population of candidate prescriptor neural network models, wherein each candidate prescriptor neural network model includes prescribed actions for a given context, the prescribed actions including recommended changes to the implementation of one or more non-pharmaceutical interventions (NPIs);

selecting a subset of candidate prescriptor neural network models from the initial population; and evaluating, using the trained predictor neural network model as a surrogate, each candidate prescriptor neural network model in the subset in accordance with an evaluation of two NPI-related factors impacted by the prescribed actions, the two NPI-related factors including an expected number of cases according to the prescribed NPIs and the total stringency of the prescribed NPIs.

* * * * *